US012673036B2

(12) United States Patent
Pantos et al.

(10) Patent No.: US 12,673,036 B2
(45) Date of Patent: *Jul. 7, 2026

(54) METHOD OF USING L-TRIIODOTHYRONINE (T3) FOR THE TREATMENT OF TISSUE HYPOXIA AND SEPSIS

(71) Applicants: UNI-PHARMA KLEON TSETIS PHARMACEUTICAL LABORATORIES S.A., Athens (GR); Ioulia Tseti, Attica (GR)

(72) Inventors: Constantinos Pantos, Kantza Pallini (GR); Iordanis Mourouzis, Korydallos (GR)

(73) Assignees: Ioulia Tseti, Attica (GR); UNI-PHARMA KLEON TSETIS PHARMACEUTICAL LABORATORIES S.A., Athens (GR)

( * ) Notice: Subject to any disclaimer, the term of this patent is extended or adjusted under 35 U.S.C. 154(b) by 729 days.

This patent is subject to a terminal disclaimer.

(21) Appl. No.: 17/920,171

(22) PCT Filed: Apr. 15, 2021

(86) PCT No.: PCT/GR2021/000019
§ 371 (c)(1),
(2) Date: Oct. 20, 2022

(87) PCT Pub. No.: WO2021/214497
PCT Pub. Date: Oct. 28, 2021

(65) Prior Publication Data
US 2023/0157982 A1 May 25, 2023

(30) Foreign Application Priority Data

| | | |
|---|---|---|
| Apr. 21, 2020 | (GR) | 20200100200 |
| Nov. 23, 2020 | (GR) | 20200100695 |
| Mar. 29, 2021 | (GR) | 20210100216 |

(51) Int. Cl.
| | |
|---|---|
| *A61K 31/198* | (2006.01) |
| *A61K 9/00* | (2006.01) |
| *A61K 47/36* | (2006.01) |
| *A61P 9/04* | (2006.01) |
| *A61P 29/00* | (2006.01) |
| *A61P 31/00* | (2006.01) |
| *A61P 31/14* | (2006.01) |

(52) U.S. Cl.
CPC .......... *A61K 31/198* (2013.01); *A61K 9/0019* (2013.01); *A61K 47/36* (2013.01); *A61P 9/04* (2018.01); *A61P 29/00* (2018.01); *A61P 31/00* (2018.01); *A61P 31/14* (2018.01)

(58) Field of Classification Search
CPC .... A61K 31/198; A61K 9/0019; A61K 47/36; A61K 31/195; A61P 31/14; A61P 29/00; A61P 9/04
See application file for complete search history.

(56) References Cited

U.S. PATENT DOCUMENTS

| | | |
|---|---|---|
| 2005/0059574 A1 | 3/2005 | Klein et al. |
| 2011/0142947 A1 | 6/2011 | Rubin et al. |

FOREIGN PATENT DOCUMENTS

| | | | |
|---|---|---|---|
| CN | 103705497 A | 4/2014 | |
| GR | 1010068 | 9/2021 | |
| GR | 1010182 | 3/2022 | |
| GR | 101026 | 6/2022 | |
| WO | 95/00135 A1 | 1/1995 | |
| WO | WO-9524919 A1 * | 9/1995 | ............ A61K 38/27 |
| WO | 02/51403 A1 | 7/2002 | |
| WO | 2017/075607 A1 | 5/2017 | |
| WO | 2020144073 | 7/2020 | |
| WO | 2021/1214497 A1 | 6/2021 | |

OTHER PUBLICATIONS

Visveswaran Gautam K et al., "Acute left ventricular dysfunction complicating pregnancy on ECMO: Tri-iodothyronine to the rescue with real time transesophageal echocardiography", Journal of Cardiology Cases, Elsevier, Amsterdam, NL, vol. 13, No. 1, Nov. 3, 2015 (Nov. 3, 2015), pp. 33-36.
Anonymous, "Triiodothyronine for the Treatment of Critically Ill Patients With COVID-19 Infection", Internet Apr. 16, 2020 (Apr. 16, 2020), pp. 1-10.
Lelubre Christophe et al., "Mechanisms and treatment of organ failure in sepsis", Apr. 24, 2018 (Apr. 24, 2018), vol. 14, No. 7, pp. 417-427.
Iordaniss Mourouzis et al., "Triiodothyronine prevents tissue hypoxia in experimental sepsis: potential therapeutic implications", Intensive Care Medicine Experimental, Biomed Central Ltd, London, UK, vol. 9, No. 1, Apr. 9, 2021 (Apr. 9, 2021), pp. 1-4.
Dekker NAM, et al. Microvascular Alterations During Cardiac Surgery Using a Heparin or Phosphorylcholine-Coated Circuit. J. Cardiothorac. Vasc. Anesth. 2020, 34 (4): 912-919.
Sakr Y, et al. Persistent microcirculatory alterations are associated with organ failure and death in patients with septic shock. Crit. Care Med. 2004, 32 (9): 1825-31.

(Continued)

*Primary Examiner* — Kevin E Weddington
(74) *Attorney, Agent, or Firm* — DILWORTH IP, LLC

(57) ABSTRACT

A method of using a composition consisting of L-triiodothyronine or a pharmaceutically acceptable salt thereof and one or more pharmaceutically acceptable excipients, for the treatment of a patient having an inflammatory response and one or multi-organ dysfunction, including kidney, liver, brain, lung, heart, gastrointestinal hematopoietic, and/or coagulatory system, due to long standing hypoxia and microvascular dysfunction, the patient having sepsis, coronavirus infection, cancer, severe trauma, and/or in heart and/or other organ transplants.

19 Claims, 16 Drawing Sheets

(56) References Cited

OTHER PUBLICATIONS

Maillet JM et al. Frequency, risk factors, and outcome of hyperlactatemia after cardiac surgery. Chest 2003, 123: 1361-6.

Abramson D et al. Lactate clearance and survival following injury. J. Trauma. 1993, 35: 584-8.

Muz et al. The role of hypoxia in cancer progression, angiogenesis, metastasis, and resistance to therapy. Hypoxia 2015, 3: 83-92.

Dekker NAM, et al. Postoperative microcirculatory perfusion and endothelial glycocalyx shedding following cardiac surgery with cardiopulmonary bypass, Anesthesia, 2019, 74: 609-618.

O'Brien J.M., et al., Sepsis, Am. J. Med. 2007, 120, pp. 1012-1022.

Klouwenberg, PK. Classification of sepsis, severe sepsis and septic shock: the impact of minor variations in data capture and definition of SIRS criteria. Intensive Care Med 2012, 38, pp. 811-819.

Nguyen, HB et al. Early lactate clearance is associated with biomarkers of inflammation, coagulation, apoptosis, organ dysfunction and mortality in severe sepsis and septic shock. J. Inflam. 2010, 7: 6.

Padhi, R., et al., Prognostic significance of nonthyroidal disease syndrome in critically ill adult patients with sepsis. Int. J. Crit. IlIn. Inj. Sci. 2018, 8: 165-172.

Ma, Shwu-Fan, et al., Type 2 Deiodinase and Host Responses of Sepsis and Acute Lung Injury Am. J. of Respir. Cell Mol. Biol., 2011, 45 (6): 1203-1211.

Yokoe, T., et al., Triiodothyronine (T3) ameliorates the cytokine storm in rats with sepsis. Crit. Care 2000, 4: 59.

Kaptein, EM, et al., Thyroid hormone therapy for postoperative nonthyroidal diseases: a systematic review and synthesis. J. Clin. Endocrinol. Metab. 2010, 95: 4526-4534.

ADVANZ Pharma, Liothyronine Sodium 20 micrograms Powder for Solution for Injection, www.medicines.org.uk/emc/product/2805/smpc#/gref, Aug. 10, 2007, 7 pages.

Pantos, C., et al., Thyroid hormone improves postischaemic recovery of function while limiting apoptosis: a new therapeutic approach to support hemodynamics in the setting of ischaemia-reperfusion? Basic Res. Cardiol. (2009) 104, 69-77; doi:10.1007/s00395-008-0758-4.

Rudski, L.G., et al., Guidelines for the echocardiographic assessment of the right heart in adults: a report from the American Society of Echocardiography endorsed by the European Association of Echocardiography, a registered branch of the European Society of Cardiology, and the Canadian Society of Echocardiography, J. Am. Soc. Echocardiogr. 2010, 23: 685-713.

Reems, M.M., et al., Central venous pressure: principles, measurement, and interpretation. Compend. Contin. Educ. Vet. 2012, 34(1):E1.

ICSH recommendations for measurement of erythrocyte sedimentation rate, J. Clin. Pathol. 1993, 46 (3): 198-203.

Harisson, M., Erythrocyte sedimentation rate and C-reactive protein, Aust. Prescr. 2015, 38 (3): 93-4.

Cho, Y.I., et al., Hemorheology and microvascular disorders, Korean Circ. J., Jun. 2011; 41(6): 287-95.

Vergote, I., et al., A randomized, double-blind, placebo-controlled phase 1b/2 study of ralimetinib, a p38 MAPK Inhibitor, plus gemcitabine and carboplatin versus gemcitabine and carboplatin for women with recurrent platinum-sensitive ovarian cancer, Gynecologic Oncology, https://doi.org/10.1016/j.ygyno.2019.11.006., (2019), 9 pages.

Newby, L. Kristin, et al., Losmapimod, a novel p38 mitogen-activated protein kinase inhibitor, in non-ST-segment elevation myocardial infarction: a randomised phase 2 trial, Lancet (2014) 384, 1187-95.

Nair, A.B. and Jacob, S., A simple practice guide for dose conversion between animals and humans, J. Basic Clin. Pharma, 2016, 7: 27-31.

Nuzzo, E., et al., Pyruvate dehydrogenase levels are low in sepsis. Crit Care, 2015, 19: P33 p. 11.

Clinical Trial Results: Triiodothyronine for the treatment of critically ill patients with COVID-19 infection (Thy-Support Study), EudraCT: 2020-001623-13.

Lapić, I, et al., Erythrocyte sedimentation rate is associated with severe coronavirus disease 2019 (COVID-19): a pooled analysis, Clin. Chem. Lab Med., 2020, 58(7): 1146-1148.

Uni-Pharma Kleon Tsetis Pharmaceutical Laboratories S.A., Triiodothyronine for the Treatment of Critically Ill Patients with COVID-19 Infection (Thy-Support), ClimincalTrials.gov, Identifier: NCT04348513, Apr. 16, 2020, 10 pages.

Visveswaran, et al., Acute left ventricular dysfunction complicating pregnancy on ECMO: Tri-iodothyronine to the rescue with real time transesophageal echocardiography, Journal of Cardiology Cases, 13 (2016) , pp. 33-36.

International Search Report and Written Opinion in related PCT/GR2021/000019; dated Aug. 9, 2021, 9 pages.

Gore, Dennis C. et al., Triiodothyronine (T3( Administration in Patients with Sepsis Induced Euthyroid Sick Syndrome: Hemodynamic and Metabolic Effects, Sepsis, 1988, pp. 163-169.

Triiodothyronine for the Treatment of Critcally Ill Patients with COVID-19 Infection, ClinicalTrials.gov, Uni-Pharma Kleon Tsetis Pharmaceutical Laboratories S.A., 2020, pp. 1-2.

Visveswaran, Gautam K. et al., Acute left ventricular dysfunction complicating pregnancy on ECMO: Tri-iodothyronine to the rescue with real time transesophageal echocardiography, Journal of Cardiology Cases, 2016, pp. 33-36.

Lelubre, Christophe, Mechanisms and treatment of organ failure in sepsis, Nature Reviews Nephrology, 2018, pp. 1-11.

First Office Action in CN Patent Application No. 202180029865.9 dated Nov. 24, 2023.

Lourbopoulos, et al., Effects of Thyroid Hormone on Tissue Hypoxia: Relevance to Sepsis Therapy, Journal of Clinical Medicine, 2021, 10, 5855,18 pages.

Pantos, et al., Acute triiodothyronine treatment and red blood cell sedimentation rate (ESR) in critically ill COVID-19 patients: A novel association?, Clinical Hemorheology and Microcirculation 79 (2021) pp. 485-488.

Pantos, et al., Effects of Acute Triiodothyronine Treatment in Patients with Anterior Myocardial Infarction Undergoing Primary Angioplasty: Evidence from a Pilot Randomized Clinical Trial (ThyRepair Study), Thyroid, vol. 32, No. 6, 2022, © Mary Ann Liebert, Inc., DOI: 10.1089/thy.2021.0596, pp. 714-724.

Iliopulou, et al., Time dependent and independent effects of thyroid hormone administration following myocardial infarction in rats, Molecular Medicine Reports, Mar. 12, 2018, 18:864-876.

Mourouzis, et al., Effects of T3 Administration on Ex Vivo Rat Hearts Subjected to Normothermic Perfusion: Therapeutic Implications in Donor Heart Preservation and Repair, Transplant International, Feb. 7, 2023, vol. 36 | Article 10742, pp. 1-10.

Mourouzis, et al., The Potential of Thyroid Hormone Therapy in Severe COVID-19: Rationale and Preliminary Evidence, International Journal of Environmental Research and Public Health, Jun. 30, 2022, 19, 8063, pp. 1-13.

Mantzouratou, et al., Thyroid Hormone and Heart Failure: Charting Known Pathways for Cardiac Repair/Regeneration, Biomedicines, Mar. 21, 2023, 11, 975, pp. 1-13.

Lervasi, et al., Thyroid and Heart, A Comprehensive Translational Essay, Second Edition, Springer Nature Switzerland, 2020, 429 pages.

Gore, et al., Triiodothyronine (T3) Administration in Patients with Sepsis Induced Euthyroid Sick Syndrome: Hemodynamic and Metabolic Effects, Sepsis 1998; 2:163-169.

Li, et al., Thyroid Hormone Protects Primary Cortical Neurons Exposed to Hypoxia by Reducing DNA Methylation and Apoptosis, Endocrinology, Oct. 1, 2019;160(10):2243-2256.

Maiden, Matthew; Tri-iodothyronine (T3)Therapy in a Pre-Clinical Model of Septic Shock, A thesis submitted for the degree of Doctor of Philosophy, Adelaide Research & Scholarship, Mar. 23, 2015, 306 pages.

Manolis, et al., Cardiovascular Complications of the Coronavirus (COVID-19) Infection, ResearchGate, Rhythmos, vol. 15, No. 2, Apr. 7, 2020, 7 pages.

Özozan, et al., Is tri-iodothyronine a better choice than activated protein C in sepsis treatment?, Ulus Travma Acil Cerrahi Derg, Nov. 2019, vol. 25, No. 6, p. 545-554.

(56)        References Cited

OTHER PUBLICATIONS

Pantos, et al., Thyroid hormone receptor a1 as a novel therapeutic target for tissue repair, Ann Transl Med, Jun. 12, 2018, 11 pages.

Pantos, et al., Triiodothyronine for the treatment of critically ill patients with COVID-19 infection: A structured summary of a study protocol for a randomised controlled trial, Trials 21, Article No. 573, Jun. 26, 2020, 3 pages.

Pantos, et al., Use of triiodothyronine to treat critically ill COVID-19 patients: a new clinical trial, Critical Care, Apr. 30, 2020, 24:209, 2 pages.

Renoux, et al., Impact of COVID-19 on red blood cell rheology, Clinical Trial, British Journal of Haematology and John Wiley & Sons Ltd., Jan. 7, 2021, 192, 4 pages.

Office Action received for Japanese Patent Application No. 2022-563957, mailed on Mar. 25, 2025, 6 pages (3 pages of English Translation and 3 pages of Original Document).

Petrov V.S., et al., Extracorporeal haemocorrection and its impact on free-radical oxidation and antioxidant defense in abdominal sepsis. Messenger of Anesthesiology and Resuscitation, 2018, vol. 15, No. 1, p. 40-45.

Makino, A. et al., Thyroid Hormone Recepton-β Is Associated with Coronary Angiogenesis during Pathological Cardiac Hypertrophy, The Endocrine Society, Endocrinology, Apr. 2009, pp. 2008-2015.

Notification of Reasons for Refusal in JP Patent Application No. 2022563957 dated Feb. 16, 2026.

De Waha, Suzzanne, et al., "Relationship between microvascular obstruction and adverse events following primary percutaneous coronary intervention for ST-segment elevation myocardial infarction: an individual patient data pooled analysis from seven randomized trials", European Heart Journal (2017) 38, pp. 3502-3510.

Decision to grant a European patent received for European Application No. 19832974.0, mailed on Feb. 23, 2023, 3 pages.

Elgendy, Islam Y., et al., "Microvascular obstruction in ST elevation myocardial infarction patients undergoing primary percutaneous coronary intervention: another frontier to conquer?", Journal of Thoracic Disease, vol. 10, No. 3, Mar. 2018, pp. 1343-1346.

Hamilton MA, Stevenson LW, Fonarow GC, Steimle A, Goldhaber JI, Child JS, Chopra IJ, Moriguchi JD, Hage A. Safety and hemodynamic effects of intravenous triiodothyronine in advanced congestive heart failure. The American journal of cardiology. Feb. 15, 1998; 81(4):443-7. (Year: 1998).

Intention to Grant received for European Application No. 19832974.0, mailed on Oct. 5, 2022, 6 pages.

International Preliminary Report on Patentability in PCT/EP2019/087056; dated Aug. 19, 2020, 10 pages.

International Search Report and Written Opinion in PCT/EP2019/087056; dated Feb. 17, 2020, 13 pages.

Khalife WI, et al. Treatment of subclinical hypothyroidism reverses ischemia and prevents myocyte loss and progressive LV dysfunction in hamsters with dilated cardiomyopathy. American Journal of Physiology-Heart and Circulatory Physiology. Dec. 2005; 289(6): H2409-15. (Year: 2005).

Mdzinarishvili, Alexander, et al., "Engineering triiodothyronine (T3) nanoparticle for use in ischemic brain stroke", Drug Deliv. and Transl. Res. (2013) 3: pp. 309-317.

Nazir, Sheraz A., "Strategies to attenuate micro-vascular obstruction during P-PCI: the randomized reperfusion facilitated by local adjunctive therapy in ST-elevation myocardial infarction trial", European Heart Journal (2016) 37, pp. 1910-1919.

Nicolini G, Forini F, Kusmic C, Pitto L, Mariani L, Iervasi G. Early and short-term triiodothyronine supplementation prevents adverse postischemic cardiac remodeling: role of transforming growth factor-ß1 and antifibrotic miRNA signaling. Molecular Medicine. Jan. 2015; 21:900-11. (Year: 2015).

Occhipinti G, Strosio M, Rinaldi R, Ruberti A, Brugaletta S. Pharmacological and Interventional Prevention and Treatment of Microvascular Obstruction Following Primary PCI in STEMI. Journal of Cardiovascular Development and Disease. Nov. 2025; 12(11):440. (Year: 2025).

Office Action received for Canadian Patent Application No. 3115896, mailed on Oct. 29, 2024, 4 pages.

Office Action received for Korean Patent Application No. 10-2022-7039203, mailed on Feb. 19, 2026, 14 pages (7 pages of English Translation and 7 pages of Original Document).

Pantos, Constantinos, et al., "Translating thyroid hormone effects into clinical practice: the relevance of thyroid hormone receptor a1 in cardiac repair", Springer Science+Business Media New York, Dec. 11, 2014, 10 pages.

Pingitore A, et al. Usefulness of triiodothyronine replacement therapy in patients with ST elevation myocardial infarction and borderline/reduced triiodothyronine levels (from the THIRST study). The American journal of cardiology. Mar. 15, 2019; 123(6):905-12. (Year: 2018).

Triiodothyronine for repair of left ventricular dysfunction and Remodeling in STEMI Patients, Ty-REPAIR clinical trial, EudraCT, URL: <https://www.clinicaltrialsregister.eu/ctr-search/trial/2016-000631-40/GR, Apr. 18, 2019.

Fracassi F, Niccoli G. Angiogenesis and microvascularobstruction: still a research topic ora new therapeutic target ?. Revista Espanola de Cardiologia (English ed.). Nov. 10, 2017;71(6):420-2. (Year: 2017).

Makino A, Suarez J, Wang H, Belke DD, Scott BT, Dillmann WH. Thyroid hormone receptor- is associated with coronary angiogenesis during pathological cardiac hypertrophy. Endocrinology. Apr. 1, 2009;150(4):2008-15. (Year: 2009).

Rajagopalan V, Zhang Y, Pol C, Costello C, Seitter S, Lehto A, Savinova OV, Chen YF, Gerdes AM. Modified low-dose triiodo-L-thyronine therapy safely improves function following myocardial ischemia-reperfusion injury. Frontiers in Physiology. Apr. 12, 2017;8:225. (Year: 2017).

Sabatino L, Kusmic C, Nicolini G, Amato R, Casini G, Iervasi G, Balzan S. T3 enhances Ang2 in rat aorta in myocardial I/R: comparison with left ventricle. Journal of Molecular Endocrinology. Jul. 21, 2016 ;57(3): 139-49. (Year: 2016).

* cited by examiner

1

METHOD OF USING L-TRIIODOTHYRONINE (T3) FOR THE TREATMENT OF TISSUE HYPOXIA AND SEPSIS

FIELD OF THE INVENTION

The present invention relates to a composition comprising L-triiodothyronine or a pharmaceutically acceptable salt thereof, for use in the treatment of inflammatory response and one or multi-organ dysfunction, including kidney, liver, brain, lung, heart, gastrointestinal hematopoietic, and/or coagulatory system, due to long standing hypoxia and microvascular dysfunction, in patients with sepsis, coronavirus infection, cancer, severe trauma, and/or in heart and/or other organ transplants.

BACKGROUND OF THE INVENTION

Microvascular dysfunction is a common cause of tissue hypoxia developed at the cellular level in several critical clinical conditions and has significant implications resulting in dysfunction and insufficiency of one or more vital organs (Dekker N A M, et al. Microvascular Alterations During Cardiac Surgery Using a Heparin or Phosphorylcholine-Coated Circuit. *J. Cardiothorac. Vasc. Anesth.* 2020, 34 (4): 912-919). Prolonged hypoxia, often resulting in organ damage, occurs because of either systemic or local mismatch between oxygen delivery and tissue demand despite normal organ blood flow. This response often occurs even though both cardiac output and blood oxygenation have been restored to normal levels (macro- to micro-circulation uncoupling).

Prolonged microvascular dysfunction and tissue hypoxia, as recorded by elevated levels of blood lactate, lead to multiple organ failure in patients with sepsis (renal, hepatic and heart damage) and is associated with increased mortality in these patients (Sakr Y, et al. Persistent microcirculatory alterations are associated with organ failure and death in patients with septic shock. *Crit. Care Med.* 2004, 32 (9): 1825-31). High levels of lactate due to hypoxia are also linked with poor outcome for patients in other critical conditions such as after heart surgery (Maillet J M et al. Frequency, risk factors, and outcome of hyperlactatemia after cardiac surgery. *Chest* 2003, 123: 1361-6) and injury after multiple trauma (Abramson D et al. Lactate clearance and survival following injury. *J. Trauma.* 1993, 35: 584-8).

Tissue hypoxia also plays a pivotal role in the development of cancer cells. Hypoxia facilitates cell survival and propagation of tumors. The role of hypoxia is two-fold: it promotes angiogenesis in order to provide oxygen and nutrients to the rapidly growing tumor and at the same time facilitates survival and proliferation of cancer cells. However, vessels due to such an angiogenesis are often abnormal and immature, frequently presenting fluid extravasation resulting in edema and afterall maintenance of hypoxia, thus creating a vicious circle between hypoxia and tumor growth (Muz et al. The role of hypoxia in cancer progression, angiogenesis, metastasis, and resistance to therapy. *Hypoxia* 2015, 3: 83-92). These findings suggest that new therapies addressing hypoxia may break this vicious cycle targeting against tumor growth as well as cancer cell metastasis.

Cardiac surgery such as coronary artery bypass graft is often associated with microvascular perfusion disturbances which persist even for 72 hours following surgery. This microvascular dysfunction creates tissue hypoxia and may play an important role in the development of postoperative heart failure resulting in prolonged hospital stay. The onset of bypass surgery is also associated with an immediate decrease in microvascular perfusion due to an acute reduction in capillary density, mainly caused by systemic inflammatory response and hemodialysis resulting in endothelial dysfunction. In addition, bypass promotes endothelial activation thus leading to increased vascular permeability and leakage leading to oedema formation, tissue swelling and further worsening of hypoxia (Dekker N A M, et al. Postoperative microcirculatory perfusion and endothelial glycocalyx shedding following cardiac surgery with cardiopulmonary bypass. *Anesthesia* 2019, 74:609-618). New treatments aiming to prevent and treat microvascular dysfunction and tissue hypoxia during cardiac surgery may be important in improving patients' outcome.

Microvascular dysfunction and tissue hypoxia development followed by consequent long-term tissue damage also play an important role in instances where extracorporeal maintenance of vital organs is required, such as in cases of heart transplantation. In general, heart preservation in transplant cases can be achieved by warm perfusion with special nutrient solutions, instead of using a cold preservation solution. Heart warm perfusion is a new and promising approach; however, it often results in long-term microvascular dysfunction and tissue hypoxia despite the successful maintenance of coronary perfusion and diastolic and systolic dysfunction of the left ventricle. Recent technological advances have significantly improved the effects of continuous warm blood perfusion ex vivo by reducing the need for myocardial ischemia in graft and implant surgeries and in heart surgeries. Clinical trials with this pioneering technology indicate its safety and effectiveness, however, it is still significantly limited due to development of microvascular dysfunction, tissue hypoxia and consequent long-term tissue damage.

Sepsis is a complex disorder which can be described as the body's extreme response to an infection and is often associated with acute multi-organ dysfunction and high mortality. Sepsis causes more than 2.8 million deaths globally per year, which accounts to 5-6% of a health system's total hospitalization costs. The World Health Organization and the World Health Summit in 2017 set sepsis as a global health priority, adopting a series of proposals and measures to improve its prevention, diagnosis, and treatment.

Following the guidelines, treatment of sepsis should begin as soon as possible after diagnosis. Within the first hour, the appropriate antibiotics should be received and at the same time relevant blood culture samples should be obtained. Stabilization of hemodynamics should be achieved within the first hour through the administration of crystalloid solutions and if necessary, the use of inotropic-vasoactive agents (noradrenaline, dopamine, adrenaline). However, despite the stabilization of macro-circulation and the restoration of oxygen in the blood, sepsis often results in multi-organ failure due to microvascular disorders and hypoxia at the cellular level. Accumulation of lactate despite the restoration of macro-circulation is highly associated with mortality and has a high prognostic value. Lactate levels represent an important indicator for both tissue ischemia at the cellular level and micro-circulatory damage. Corticosteroids may inhibit the maladaptive inflammatory response associated with sepsis, however, recent data shows that there is no significant effect on survival. Thus, hydrocortisone is only recommended when sepsis-induced hemodynamic instability cannot be adequately treated with fluid and vasoactive agents.

Sepsis can also cause secondary damages in organs. Specifically, 40-50% of septic patients present renal failure, 35% present hepatic failure, 6-9% present secondary respiratory failure, 34% present secondary leukopenia and immunosuppression, while the rates of secondary cardiac, cerebral and gastrointestinal disorders may vary. Secondary damage of the coagulatory system which is responsible for increased rates of thrombosis is also reported.

Sepsis can be caused by a variety of infections such as bacterial (e.g., pneumococcus, meningococcus, *Staphylococcus aureus, Haemophilus, Pseudomonas aeruginosa*, etc.), viral (e.g., influenza, Ebola, coxsackie, SARS-Cov-2, etc.), parasitic (e.g., *Schistosoma*, amoeba, etc.), as well as fungal (e.g., *Aspergillus, Cryptococcus, Histoplasma*, etc.) (O'Brien J. M. et al. Sepsis. *Am. J. Med.* 2007, 120:1012-1022). Respiratory and intra-abdominal infections are the most common associated sites of infection, following the urinary system, the central nervous system and the soft tissues or bones. Sometimes, the infection may simply be found in the blood or involve injuries or burns (Klouwenberg, P K. Classification of sepsis, severe sepsis and septic shock: the impact of minor variations in data capture and definition of SIRS criteria. Intensive Care Med 2012, 38:811-819).

Mechanisms implicated in sepsis-induced cell damage and organ dysfunction are not fully understood and continue to be an active field of scientific research. Tissue ischemia occurs either due to systemic or local disturbance in the balance between oxygen transport and tissue demand. Therefore, the main reasons of sepsis-induced multi-organ failure are the reduction of perfusion and oxygenation of the organs and the microvascular dysfunction leading to hypoxia at the cellular level even after apparent restoration of stable systemic hemodynamics.

It is important to mention that even after the aggressive restoration of the septic patient's circulation, by achieving a normal or high cardiac output, tissue perfusion at the cellular level remains largely problematic. This indicates that sepsis-induced tissue hypoxia is essentially a problem of the micro-circulation. Indeed, the perfusion of small vessels is strongly associated with sepsis prognosis.

Several studies have shown that tissue hypoxia, which is recorded as an insufficient lactate clearance in the blood in the first hours of patient's recovery, is associated with multiorgan failure and increased mortality (Nguyen, H B et al. Early lactate clearance is associated with biomarkers of inflammation, coagulation, apoptosis, organ dysfunction and mortality in severe sepsis and septic shock. *J. Inflam.* 2010, 7:6). Another study showed that there is a strong correlation between the improvement of lactate levels in the first 6 hours and a consequent improvement of blood biomarkers over 72 hours as well as improvement of multi-organ dysfunction. It should be noted that lactate clearance has been strongly associated with improved micro-circulation. These findings suggest that tissue hypoxia is a primary factor playing a critical role in the pathophysiological mechanisms of sepsis in multi-organ failure and not an end-stage phenomenon. Interestingly, tissue hypoxia in severe sepsis is also associated with increased apoptosis. In particular, caspase-3, a key indicator of apoptosis pathway, is found to be much higher after 72 hours in septic patients with reduced lactate clearance compared with patients with increased lactate clearance. In addition, tissue hypoxia seems to be a precursor to pre-thrombotic condition in severe sepsis, therefore, any treatments for tissue hypoxia may reverse hypercoagulability.

Furthermore, sepsis places the body under severe stress and leads to a neuro-hormonal response with significant physiological outcomes such as changes in thyroid hormone metabolism resulting in low serum T3 levels with normal T4 levels in less severe cases or in low serum levels for both T3 and T4 in the most severe cases. This response is known as Non-thyroid Illness Syndrome (NTIS) and appears to be an important prognostic factor for the survival of septic patients. This deregulation is known in severe acute pathological conditions such as sepsis, myocardial infarction, etc. and is associated with high mortality in sepsis (Padhi, R. et al. Prognostic significance of nonthyroidal disease syndrome in critically ill adult patients with sepsis. *Int. J. Crit. Illn. Inj. Sci.* 2018, 8:165-172). In addition, laboratory animals genetically modified to express reduced levels of deiodinase 2 (DIO2), which regulates the synthesis of biologically active T3, showed increased levels of respiratory failure in an experimental sepsis model (Ma, Shwu-Fan et al. Type 2 Deiodinase and Host Responses of Sepsis and Acute Lung Injury *Am. J. Respir. Cell Mol. Biol.* 2011, 45 (6):1203-1211.). In rat sepsis models, T3 administration was found to maintain lung function and surfactant synthesis, reduce cytokine storm and improve survival (Yokoe, T. et al. Triiodothyronine (T3) ameliorates the cytokine storm in rats with sepsis. *Crit. Care* 2000, 4:59).

So far, there are no effective treatments against microvascular dysfunction and tissue hypoxia, targeting to limit multi-organ damage due to sepsis or other pathological conditions.

Especially, there are no effective treatments against microvascular dysfunction and tissue hypoxia resulting in regulation of the inflammatory response and improvement of cardiovascular and coagulatory system dysfunction, in sepsis and other pathological conditions, and in particular in sepsis due to a coronavirus infection.

L-triiodothyronine (T3) is already tested as a drug for critically ill patients by increasing cardiac output and supporting hemodynamics. However, because of the widely established belief that T3 can lead to increased oxygen consumption and worsen hypoxia, its use is limited only to the treatment of hypothyroidism. Even in this case, it is sparingly used as a second choice behind levothyroxine (Kaptein, E M et al. Thyroid hormone therapy for postoperative nonthyroidal diseases: a systematic review and synthesis. *J. Clin. Endocrinol. Metab.* 2010, 95:4526-4534). Furthermore, it should be mentioned that the Summary of Product Characteristics (SmPC) for L-triiodothyronine solutions states that T3 is contraindicated in patients with cardiovascular disorders or angina, and may be used with extreme caution in patients with coronary heart disease (www.medicines.org.uk/emc/product/2805/smpc#gref).

On a side note, the potential effect of early administration of high dose TH (acute treatment) after an index event has been already investigated in experimental models of ischemic-reperfusion using isolated rat heart preparations. Thus, T3 administered in high doses after reperfusion improves postischaemic recovery of function while limits apoptosis [Pantos C, et al. Thyroid hormone improves postischaemic recovery of function while limiting apoptosis: a new therapeutic approach to support hemodynamics in the setting of ischaemia-reperfusion? *Basic Res. Cardiol.* (2009) 104, 69-77; doi:10.1007/s00395-008-0758-4]. In this study, the effects of T3 on reperfusion injury in a Langendorff-perfused rat heart model of 30 min zero-flow perfusion (simulating acute ischemia) and 60 min of reperfusion with or without T3 (40 µg/L) was investigated. Furthermore, phosphorylated levels of intracellular kinases were measured at time intervals of 5, 15 and 60 minutes of reperfusion. It was shown that T3 markedly improved post-ischaemic recovery of cardiac function, while at the same time acute p38 MAPK activation during the first minutes of reperfusion was significantly lowered. In particularly, phospho-p38 MAPK levels were found to be 2.3-foldless in T3 treated rats after 5 minutes as compared to the corresponding control rats and 2.1-fold less after 15 minutes, P<0.05. This may constitute a paradigm of a positive inotropic agent with anti-apoptotic action suitable for supporting hemodynamics in the clinical setting of ischaemia-reperfusion.

In addition, Document WO 2020/144073 reports the effects of high-dose T3 treatment intravenously starting immediately after reperfusion and continuing for 48 hours in patients with anterior or anterolateral ST-segment-elevation myocardial infarction (STEMI) undergoing Primary Percutaneous Coronary Intervention (PPCI). This study also explores the potential effects of 13 treatment on infarct size and cardiac remodeling by assessing changes in left ventricular (LV) volumes and geometry.

We surprisingly realized that administration of T3 in high doses, above any consideration of a thyroid replacement therapy, inhibits tissue hypoxia caused by microvascular dysfunction in various organs, including kidneys, liver, heart, lungs, brain, gastrointestinal tract, hematopoietic and coagulatory system, and reduces lactate levels. This is in contrast to the popular belief that thyroid hormone is detrimental in hypoxia due to increased oxygen consumption.

BRIEF DESCRIPTION OF THE DRAWINGS

The subject matter of the present disclosure will be more fully understood from the following detailed description, taken in connection with the accompanying drawings, in which.

SUMMARY OF THE INVENTION

Figure 1:
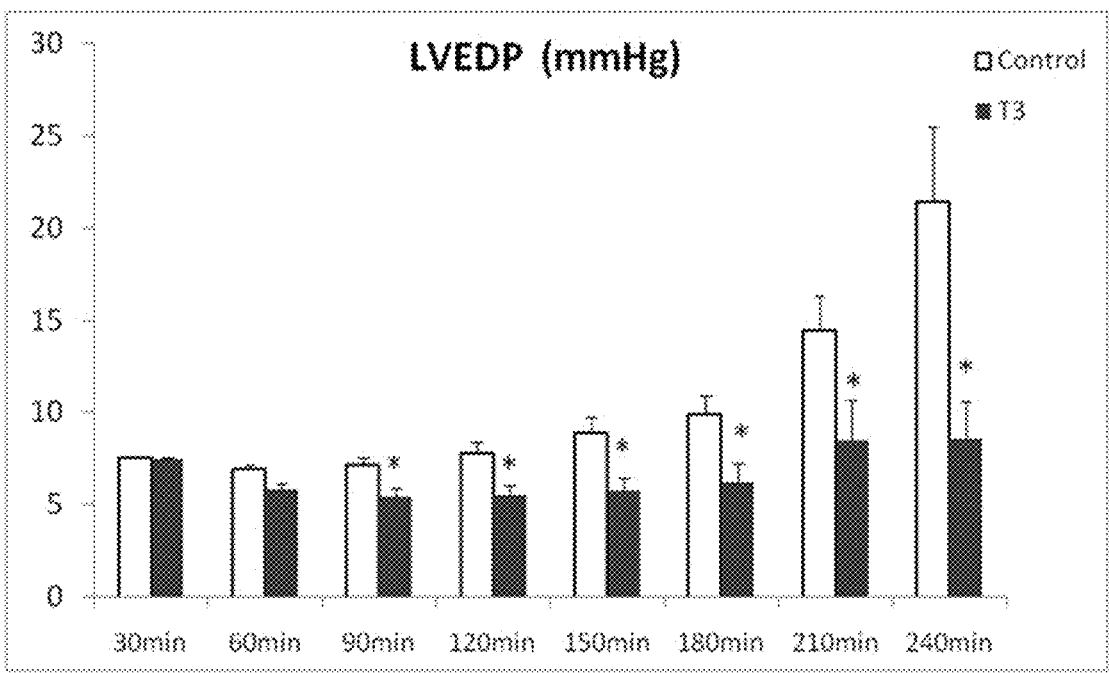
FIG. 1 shows the left ventricular end-diastolic pressure (LVEDP) under hypoxic organ perfusion conditions in normal (Control) and 13 treated hearts (T3) over 4 hours. *p<0.05 vs Control.

In the present invention, we provide strong and unprecedented evidence showing that the active form of thyroid hormone, L-triiodothyronine (T3), in high doses can treat tissue hypoxia related to microvascular dysfunction occurring in various critical pathological conditions in vital organs and systems, especially those concerning the cardiovascular system, the immune system and the coagulatory system, in particular when caused by coronavirus infection.

DETAILED DESCRIPTION OF THE INVENTION

Priority Document GR 20200100200, which is incorporated herein by reference, indicates that administration of high-dose T3 to critically ill patients with coronavirus, is an effective treatment to reduce hypoxic tissue damage and to maintain normal function of patient's vital organs.

Priority Document GR 20200100695, which is incorporated herein by reference, indicates that administration of high dose of a pharmaceutical composition containing L-triiodothyronine is beneficial in treating one or multi-organ failure in patients with tissue hypoxia and microvascular dysfunction due to sepsis, corona virus infection, cancer, severe injury or vital organ transplant.

Priority Document GR 20210100216, which is incorporated herein by reference, indicates that administration of high dose of a pharmaceutical composition containing L-triiodothyronine is effective in the treatment of inflammatory response and cardiovascular failure especially due to long standing hypoxia and microvascular dysfunction due to sepsis.

The present invention is based on the surprising observation that administration of a dosage regimen as considered in the present invention (high-dose of T3 above any consideration of a thyroid replacement therapy), effectively treats the dysfunction of one or more vital organs in patients with sepsis. The present invention in particular concerns a pharmaceutical composition comprising L-triiodothyronine or a pharmaceutically acceptable salt thereof, which is administered in doses from 5 µg per Kg of body weight to 9 µg per Kg body weight, preferably from 6 µg per Kg body weight to 8 µg per Kg of body weight, most preferably 7 µg per Kg of body weight in total, during an initial period of 24-72 hours, preferably for 48 h.

The present invention is based on the surprising observation that administration of a dosage regimen as considered in the present invention (high-dose of T3 above any consideration of a thyroid replacement therapy), effectively treats cancer in one or more organs.

The present invention is based on the surprising observation that administration of a dosage regimen as considered in the present invention (high-dose of T3 above any consideration of a thyroid replacement therapy), effectively treats the dysfunction of one or more vital organs in patients with open or internal injuries.

The present invention is based on the surprising observation that administration of a dosage regimen as considered in the present invention (high-dose of T3 above any consideration of a thyroid replacement therapy), effectively treats the dysfunction of one or more vital organs in patients after heart and/or other organ transplantation.

The present invention is based on the surprising observation that administration of a dosage regimen as considered in the present invention (high-dose of T3 above any consideration of a thyroid replacement therapy), effectively treats microvascular dysfunction and tissue hypoxia due to sepsis.

The present invention is based on the surprising observation that administration of a dosage regimen as considered in the present invention (high-dose of T3 above any consideration of a thyroid replacement therapy), effectively treats kidney failure caused by tissue hypoxia due to microvascular dysfunction.

The present invention is based on the surprising observation that administration of a dosage regimen as considered in the present invention (high-dose of T3 above any consideration of a thyroid replacement therapy), effectively treats liver failure caused by tissue hypoxia due to microvascular dysfunction.

The present invention is based on the surprising observation that administration of a dosage regimen as considered in the present invention (high-dose of T3 above any consideration of a thyroid replacement therapy), effectively treats brain damage caused by tissue hypoxia due to microvascular dysfunction.

The present invention is based on the surprising observation that administration of a dosage regimen as considered in the present invention (high-dose of T3 above any consideration of a thyroid replacement therapy), effectively treats hematopoietic system failure caused by tissue hypoxia due to microvascular dysfunction.

The present invention is based on the surprising observation that administration of a dosage regimen as considered in the present invention (high-dose of T3 above any consideration of a thyroid replacement therapy), effectively treats gastrointestinal tract failure caused by tissue hypoxia due to microvascular dysfunction.

The present invention is based on the surprising observation that administration of a dosage regimen as considered in the present invention (high-dose of T3 above any consideration of a thyroid replacement therapy), effectively treats respiratory system failure caused by tissue hypoxia due to microvascular dysfunction.

The present invention is based on the surprising observation that administration of a dosage regimen as considered in the present invention (high-dose of T3 above any consideration of a thyroid replacement therapy), effectively treats heart failure caused by tissue hypoxia due to microvascular dysfunction.

The present invention is based on the surprising observation that administration of a dosage regimen as considered in the present invention (high-dose of T3 above any consideration of a thyroid replacement therapy), is effective in treating tissue hypoxia due to microvascular dysfunction in a heart exposed to stress as in transplantations or heart surgeries.

The present invention is based on the surprising observation that administration of a dosage regimen as considered in the present invention (high-dose of T3 above any consideration of a thyroid replacement therapy), effectively treat microvascular dysfunction and tissue hypoxia caused by long-term ex vivo heart or other organ perfusion. This allows long-term preservation of an extracorporeal organ, thus preventing any significant tissue damage during transfer, furthermore, allows the resuscitation of heart transplants that otherwise might be unsuitable for transplantation. This is also beneficial to the overall availability of transplants.

The present invention is based on the surprising observation that administration of a dosage regimen as considered in the present invention (high-dose of T3 above any consideration of a thyroid replacement therapy), is beneficial in the extracorporeal long-term maintenance of cardiac transplants in continuous warm perfusion devices as well as in patients during cardiac surgery, thus avoiding microvascular dysfunction and myocardial tissue hypoxia.

The present invention is based on the surprising observation that administration of a dosage regimen as considered in the present invention (high-dose of T3 above any consideration of a thyroid replacement therapy), effectively treats the inflammatory response and multi-organ failure in critically ill patients with sepsis and/or coronavirus infection.

The present invention is based on the surprising observation that administration of a dosage regimen as considered in the present invention (high-dose of T3 above any consideration of a thyroid replacement therapy), effectively treats the deterioration of left and right ventricular function in critically ill patients with sepsis and/or coronavirus infection.

The present invention is based on the surprising observation that administration of a dosage regimen as considered in the present invention (high-dose of T3 above any consideration of a thyroid replacement therapy), improves the right ventricular systolic function in critically ill patients with sepsis and/or coronavirus infection.

The present invention is based on the surprising observation that administration of a dosage regimen as considered in the present invention (high-dose of T3 above any consideration of a thyroid replacement therapy) in critically ill patients diagnosed with single or multi organ dysfunction due to coronavirus infection, facilitates weaning from cardiorespiratory support. Successful weaning is defined as no requirement for ventilatory support after extubation (mechanical support) or support from extracorporeal membrane oxygenation (ECMO) for 48 hours.

The present invention further relates to the administration of a high dosage regimen of T3 to patients diagnosed with corona virus disease in combination with parallel therapeutic treatment comprising other active agents selected among Chloroquine and/or Colchicine and/or Remdesivir and/or Ralimetinib and/or Losmapimod.

So far, there is no prior art suggesting a treatment of single- or multi-organ damage from prolonged continuous hypoxia conditions, i.e., for more than 30 minutes, preferably more than 3 hours up to several days, for example till successful weaning or end of follow-up and for a time period of 30 days maximum.

Furthermore, there is not a single notion in the prior art suggesting a high-dose T3 treatment of a patient in intensive care units suffering from single or multi organ dysfunction induced by coronavirus infection.

Likewise, there is no reference in the prior art suggesting a high-dose 13 treatment of a patient in intensive care units suffering from single or multi organ dysfunction induced by COVID-19.

Unexpectedly, it was found that a high-dose T3 administration to critically ill patients with coronavirus infection represents an effective treatment to reduce hypoxic tissue injury and preserve organs' function.

Overall, the current invention relates to the surprising findings that T3 administration at high dosage under prolonged hypoxic organ perfusion conditions preserves organ function.

It is another object of the invention, a high dosage L-triiodothyronine treatment reducing excessive inflammation in critically ill patients with coronavirus infection.

It is another object of the invention, a high dosage L-triiodothyronine treatment reducing virus induced tissue injury due to virus entry and replication in critically ill patients with coronavirus infection.

It is an object of the invention, a high dosage L-triiodothyronine treatment in order to facilitate faster weaning from cardiorespiratory support in critically ill patients with coronavirus infection.

It is an object of the invention, a high dosage L-triiodothyronine treatment reducing mortality in critically ill patients with coronavirus infection.

The present invention in particular concerns a medicament comprising L-triiodothyronine administered to critically ill patients due to coronavirus and require mechanical respiratory support or extracorporeal membrane oxygenation (ECMO).

For example, a specific embodiment is the heart, wherein high dose T3 administration prevents diastolic and microvascular dysfunction and improves contractile force. Furthermore, these effects are associated with inhibition of prolonged p38 MAPK activation, which is associated with antiapoptotic action and preservation of the tissue from injury.

The present invention is based on the surprising observation that administration of a dosage regimen as considered in the present invention (high-dose of T3 above any consideration of a thyroid replacement therapy), improves the right ventricular systolic function in critically ill patients with sepsis and/or coronavirus infection, so that the parameter of Tricuspid Annular Plane Systolic Excursion (TAPSE) is preferably between 16 and 30 mm, more preferably between 20 and 25 mm. TAPSE is easily measured by an echocardiogram from the tricuspid valve annular plane and evaluates right ventricular function along the longitudinal axis. TAPSE correlates well with the general function of the right ventricle (Rudski L G et al. Guidelines for the echocardiographic assessment of the right heart in adults: a report from the American Society of Echocardiography endorsed by the European Association of Echocardiography, a registered branch of the European Society of Cardiology, and the Canadian Society of Echocardiography. *J. Am. Soc. Echocardiogr.* 2010, 23: 685-713).

The present invention is based on the surprising observation that administration of a dosage regimen as considered in the present invention (high-dose of T3 above any consideration of a thyroid replacement therapy), improves the right ventricular systolic function in critically ill patients with sepsis and/or coronavirus infection, so that the value of central venous pressure is preferably measured between 1 and 10 mm Hg, most preferably between 3.7 and 7.4 mm Hg. Central venous pressure reflects the pressure of the right atrium of the heart and is considered as an efficient indicator of right ventricular function in combination with fluid status in patients with sepsis (Reems, M. M. et al. Central venous pressure: principles, measurement, and interpretation. *Compend. Contin. Educ. Vet.* 2012, 34(1):E1).

The present invention is based on the surprising observation that administration of a dosage regimen as considered in the present invention (high-dose of T3 above any consideration of a thyroid replacement therapy), improves inflammation and coagulatory system failure, in critically ill patients with sepsis and/or coronavirus infection, so that the erythrocyte sedimentation rate is reduced by 50% over a period of 48 hours and measured preferably below 30 mm within the first hour, as calculated by the reference method described by the International Committee for Standardization in Haematology (ICSH recommendations for measurement of erythrocyte sedimentation rate. J. Clin. Pathol. 1993, 46 (3): 198-203). The erythrocyte sedimentation rate is a simple blood test measuring how quickly red blood cells settle to the bottom of an elongated vial due to gravity. It is calculated by measuring the distance (in mm) covered by red blood cells within 1 hour. It is a general indicator of inflammation and is directly affected by disorders of the coagulatory system (Harisson, M. Erythrocyte sedimentation rate and C-reactive protein. *Aust. Prescr.* 2015, 38 (3): 93-4).

Reduction of erythrocyte sedimentation rate is also linked to the function of microcirculation. The flow of blood in microvessels depends on viscous shear forces due to low flow velocities. Accordingly, when the attractive forces between erythrocytes (represented by the erythrocyte sedimentation rate) are greater than the shear force produced by microvascular flow, tissue perfusion itself cannot be sustained, leading to capillary loss. Thus, reduction of increased erythrocyte sedimentation rate indicates improved blood viscosity and better microvascular flow (Cho Y I, et al. Hemorheology and microvascular disorders. *Korean Circ J.* 2011 June; 41(6):287-95.)

The present invention is based on the surprising observation that administration of a dosage regimen as considered in the present invention (high-dose of T3 above any consideration of a thyroid replacement therapy), does not increase or even reduces the d-dimers levels, which represent an indicator to diagnose intravascular coagulopathy and thrombosis, in critically ill patients with coronavirus infection.

The present invention is based on the surprising observation that administration of a dosage regimen as considered in the present invention (high-dose of T3 above any consideration of a thyroid replacement therapy), reduces mortality in critically ill patients with tissue hypoxia and sepsis.

The present invention is based on the surprising observation that administration of a dosage regimen as considered in the present invention (high-dose of T3 above any consideration of a thyroid replacement therapy), facilitates faster weaning from cardiorespiratory support in critically ill patients with tissue hypoxia and sepsis.

The present invention is based on the surprising observation that administration of a dosage regimen as considered in the present invention (high-dose of T3 above any consideration of a thyroid replacement therapy), facilitates early discharge from Intensive Care Unit in critically ill patients due to tissue hypoxia and sepsis.

The present invention is based on the surprising observation that administration of a dosage regimen as considered in the present invention (high-dose of T3 above any consideration of a thyroid replacement therapy), facilitates early hospital discharge in critically ill patients due to tissue hypoxia and sepsis.

The present invention relates to a composition comprising L-triiodothyronine or a pharmaceutically acceptable salt thereof, for use in the treatment of inflammatory response and one or multi-organ dysfunction, including kidney, liver, brain, lung, heart, gastrointestinal, hematopoietic and/or coagulatory system, due to long standing tissue hypoxia and microvascular dysfunction, in patients with sepsis, coronavirus infection, cancer, severe trauma, and/or in heart and/or other organ transplants.

The present invention in particular concerns a pharmaceutical composition comprising L-triiodothyronine or a pharmaceutically acceptable salt thereof, which is administered following any of the commonly used routes of administration, for example, orally, parenterally, intramuscularly, intravenously, rectally, through inhalation, most preferably is administered intravenously.

The present invention in particular concerns a pharmaceutical composition comprising L-triiodothyronine or a pharmaceutically acceptable salt thereof, which is formulated either as an injectable solution for immediate administration or as a lyophilized powder for reconstitution just prior to use.

The present invention in particular concerns a pharmaceutical composition comprising L-triiodothyronine or a pharmaceutically acceptable salt thereof, which is administered intravenously as a solution with a concentration in the range between 2 to 20 µg T3/mL, preferably between 5 to 15 µg T3/mL, more preferably between 7 to 12 µg T3/mL, most preferably is 10 µg T3/mL.

In a preferred embodiment, the pharmaceutical composition comprising L-triiodothyronine or a pharmaceutically acceptable salt thereof, is in the form of a 10 µg mL T3 solution for injection in a vial containing 150 µg T3 in a total volume of 15 mL.

The present invention in particular concerns a pharmaceutical composition comprising L-triiodothyronine or a pharmaceutically acceptable salt thereof, comprising the active substance and pharmaceutically acceptable excipients among sugars, pH regulators and solvents.

In a preferred embodiment, the pharmaceutical composition comprising L-triiodothyronine or a pharmaceutically acceptable salt thereof, is comprising sodium liothyronine, dextran, sodium hydroxide 1N solution and water for injection.

In a preferred embodiment, the pharmaceutical composition comprising L-triiodothyronine or a pharmaceutically acceptable salt thereof, is in the form of a lyophilized powder for reconstitution with water for injection or sodium chloride solution 0.9%, just before its use.

The present invention in particular concerns a pharmaceutical composition comprising L-triiodothyronine or a pharmaceutically acceptable salt thereof, which is administered in doses much higher than in the normal treatment of patients with non-adequate thyroid functions (e.g., patients with hypothyroidism or myxedema).

The present invention in particular concerns a pharmaceutical composition comprising L-triiodothyronine or a pharmaceutically acceptable salt thereof, which is administered in doses from 5 µg per Kg of body weight to 9 µg per Kg body weight, preferably from 6 µg per Kg body weight to 8 µg per Kg of body weight, most preferably 7 µg per Kg of body weight in total over 24 to 72 hours, optimally for 48 hours. Without bound to any theory, a period of 24 hours is considered the minimum time frame in order to achieve the beneficial effect of this treatment, while a period of more than 72 hours does not offer any additional beneficial effect.

According to the present invention, subjects between 60 and 80 Kg can receive intravenously from 420 µg to 560 µg T3 in total.

In a preferred embodiment, a subject of 75 Kg receives intravenously from 375 µg to 675 µg T3 in total, preferably from 450 µg to 600 µg T3, most preferably 525 µg T3 in total.

According to the present invention, the pharmaceutical composition comprising L-triiodothyronine or a pharmaceutically acceptable salt thereof, is administered to a subject by continuous infusion at a rate from 0.08 to 0.20 µg/kg/h, preferably from 0.12 to 0.16 µg/kg/h and most preferably 0.14 µg/kg/h for 48 hours.

According to the present invention, the pharmaceutical composition comprising L-triiodothyronine or a pharmaceutically acceptable salt thereof, is administered to a subject as an initial bolus in the range from 0.6 µg/kg to 1.0 µg/kg body weight, preferably as an initial bolus of 0.8 µg/kg body weight, followed by continuous infusion in a rate from 0.1 to 0.2 µg/kg/h, preferably from 0.1 to 0.12 µg/kg/h and most preferably in a rate of 0.112 µg/kg/h for 48 hours.

According to the present invention, the pharmaceutical composition comprising L-triiodothyronine or a pharmaceutically acceptable salt thereof, is administered to a subject preferably as an initial bolus followed by continuous infusion than as a continuous infusion from the beginning, in order to achieve rapid onset of action and therapeutic effects. Failure to timely achieve high T3 levels can offset the favorable effects of the pharmaceutical composition.

The present invention in particular concerns a pharmaceutical composition comprising L-triiodothyronine or a pharmaceutically acceptable salt thereof, for use in the treatment of tissue hypoxia due to microvascular dysfunction, not only for short standing hypoxia, but also for long-standing hypoxia, at least 30 minutes, or at least 3 hours, or at least 4, 6, 12, 18, or 24 hours hypoxia.

EXAMPLES

The present invention is further explained by the following illustrative, non-limiting, examples.

Example 1. T3 and Prevention of Prolonged Hypoxia-Induced Injury

Figure 2:
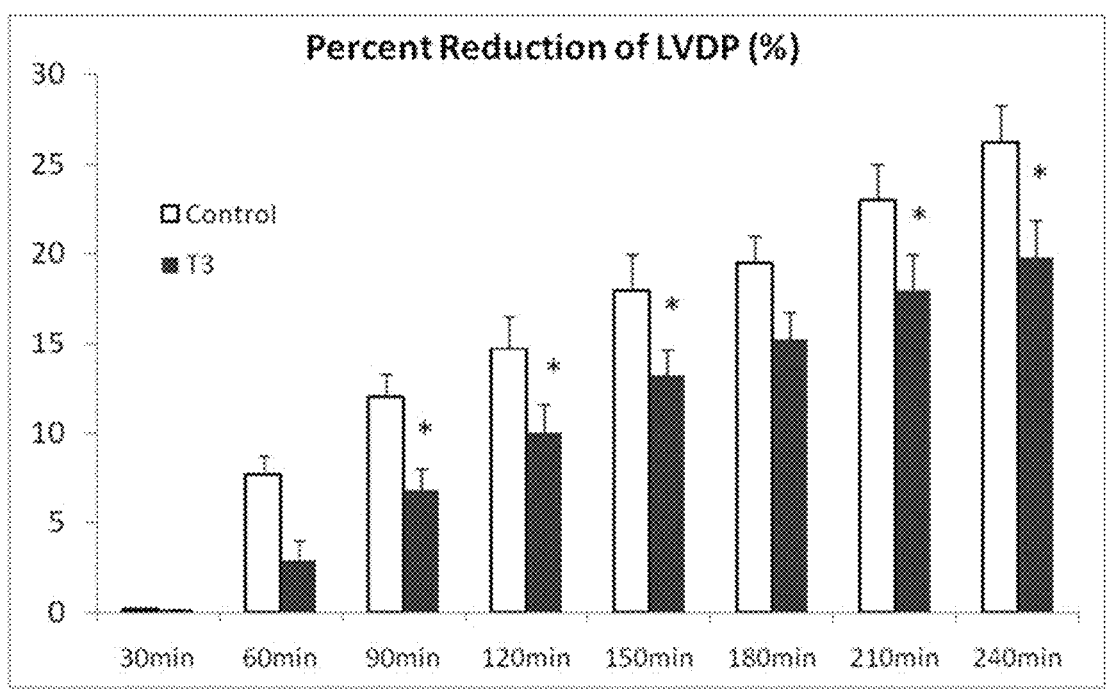
FIG. 2 shows the reduction of left ventricular developed pressure (LVDP) under hypoxic organ perfusion conditions in normal (Control) and T3 treated hearts (T3) over 4 hours. *p<0.05 vs Control.

The isolated rat heart model was used to simulate non-ischemic conditions of tissue hypoxia ex vivo. In this study, rat hearts were only perfused with oxygenated Krebs buffer containing electrolytes and glucose under normothermia. Despite normal perfusion, the organ gradually develops significant dysfunction over hours due to the absence of erythrocytes and hemoglobin that create hypoxic conditions. Thus, during a prolonged period of 4 hour hypoxic perfusion, normal hearts (Control group) gradually developed diastolic dysfunction and left ventricular end-diastolic pressure (LVEDP) substantially increased above 20 mmHg (FIG. 1). It should be noted that such an increase in LVEDP may lead to pulmonary edema in vivo. Furthermore, the force of contraction was reduced as evident by a 25% decrease in left ventricular developed pressure (LVDP) in Control hearts (FIG. 2).

Figure 3:
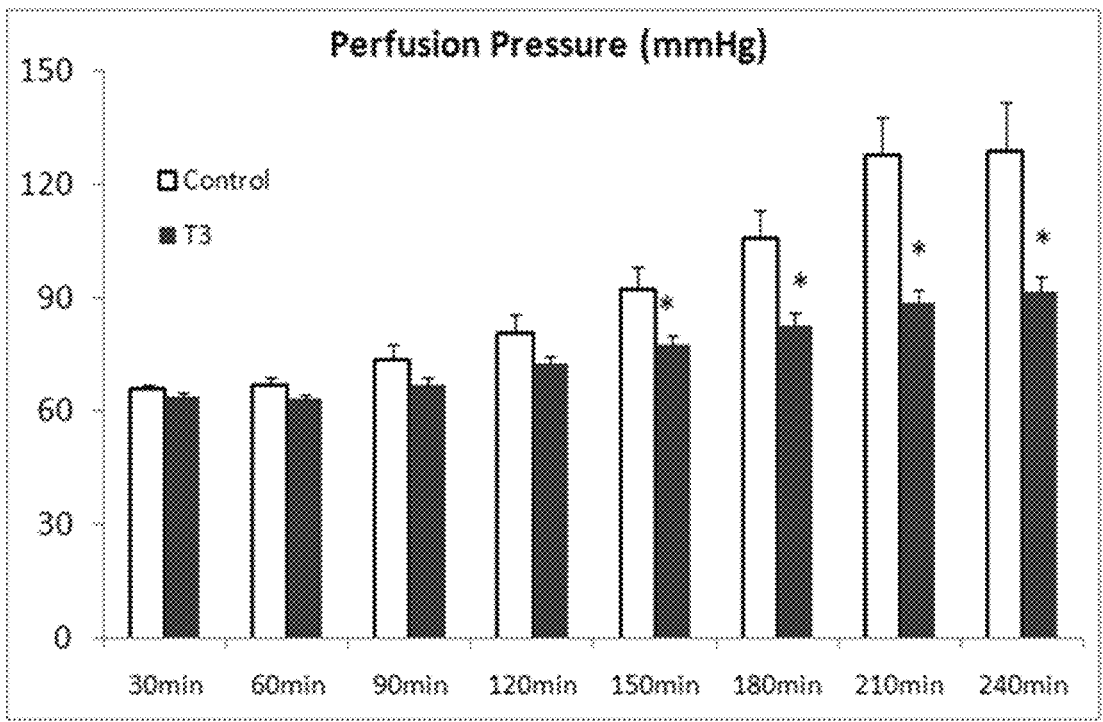
FIG. 3 shows the perfusion pressure under hypoxic organ perfusion conditions in normal (Control) and T3 treated hearts (T3) over 4 hours. *p<0.05 vs Control.
Figure 4:
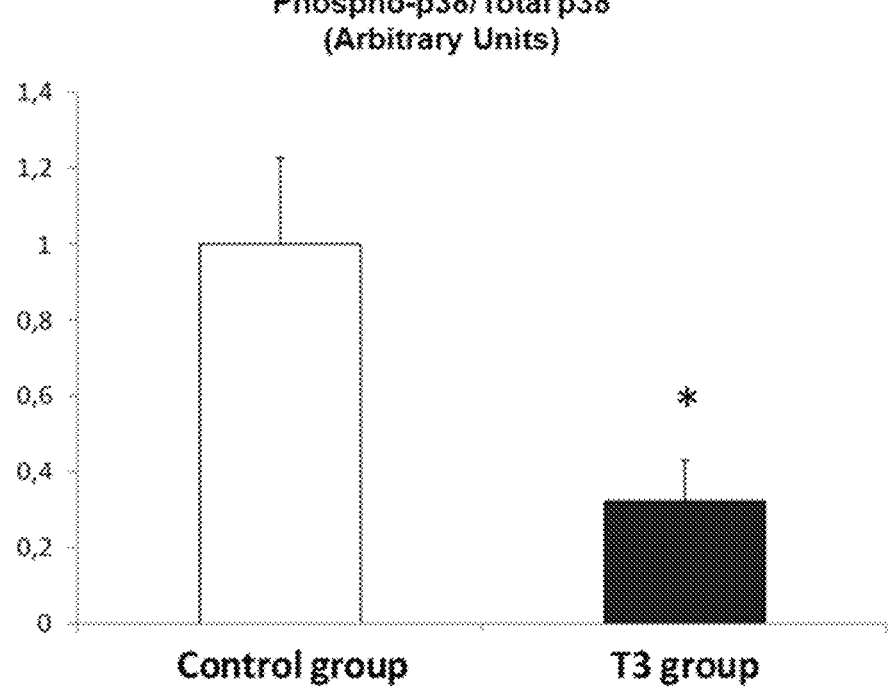
FIG. 4 shows the activation of p38 MAPK under hypoxic organ perfusion conditions in normal (Control) and T3 treated hearts (T3). *p<0.05 vs Control.

Interestingly, treatment with L-triiodothyronine (T3 group) at high doses (40 µg/L) after the first 30 min of hypoxic perfusion, attenuated diastolic dysfunction, maintained LVEDP at normal values and improved force of contraction after 4 hours. Furthermore, hypoxic perfusion resulted in microvascular dysfunction of the heart which was monitored as a significant increase in perfusion pressure of coronary vessels over time in Control hearts (FIG. 3). However, treatment with triiodothyronine significantly inhibited microvascular dysfunction and resulted in lower perfusion pressure after 4 hours (FIG. 3). Most importantly, molecular analysis of intracellular kinase signaling activation revealed that pro-apoptotic p38 MAPK was significantly activated after 4 hours of prolonged hypoxic perfusion and T3 administration prevented this activation by 3-fold, $p < 0.05$ (FIG. 4).

Specific p38 MAPK inhibitors exist and have been tested for other indications but not for prolonged hypoxic tissue injury. Ralimetinib is a selective small-molecule inhibitor of p38 MAPK. Preclinical studies have demonstrated antineoplastic activity in xenograft models as a single agent (non-small cell lung, multiple myeloma, breast, glioblastoma, and ovary) and in combination with other chemotherapeutic agents. [Vergote, I., et al., A randomized, double-blind, placebo-controlled phase 1b/2 study of ralimetinib, a p38 MAPK inhibitor, plus gemcitabine and carboplatin versus gemcitabine and carboplatin for women with recurrent platinum-sensitive ovarian cancer, *Gynecologic Oncology*, https://doi.org/10.1016/j.ygyno.2019.11.006]. Losmapimod, is another potential inhibitor of the p38 MAPK in macrophages, myocardium, and endothelial cells and presented myocardial protective effects in patients with non-ST-segment elevation myocardial infarction [I. K. Newby et al. Losmapimod, a novel p38 mitogen-activated protein kinase inhibitor, in non-ST-segment elevation myocardial infarction: a randomised phase 2 trial, Lancet (2014) 384, 1187-95].

The above-indicated results are better understood with reference to FIGS. 1 to 4.

FIG. 1 shows the left ventricular end-diastolic pressure (LVEDP) under hypoxic organ perfusion conditions in normal (Control) and T3 treated hearts (T3) over 4 hours. $*p < 0.05$ vs Control FIG. 2 shows the reduction of left ventricular developed pressure (LVDP) under hypoxic organ perfusion conditions in normal (Control) and 13 treated hearts (T3) over 4 hours. $*p < 0.05$ vs Control FIG. 3 shows the perfusion pressure under hypoxic organ perfusion conditions in normal (Control) and T3 treated hearts (T3) over 4 hours. $*p < 0.05$ vs Control FIG. 4 shows the activation of p38 MAPK under hypoxic organ perfusion conditions in normal (Control) and T3 treated hearts (T3). $*p < 0.05$ vs Control

Example 2. L-Triiodothyronine and Tissue Hypoxia in Sepsis Occurring in Myocardium, Kidneys and Liver The effect of T3 administration in high dosages in the treatment of tissue hypoxia due to microvascular dysfunction occurring in the myocardium, kidneys and liver is evaluated in a sepsis experimental model using male C57BL/6N mice of 10-12 weeks age. The animal studies were carried out in compliance with all necessary regulations in force.

The simulation of the clinical conditions during sepsis leading to tissue hypoxia and microvascular dysfunction is achieved following the most widely used clinical model of cecal ligation and puncture (CLP). In this experimental model, ligation distal to the ileocecal valve (25% of total cecum length) and perforation by a single 21 G puncture is performed under sevoflurane anesthesia causing leakage of fecal contents into the peritoneum, with subsequent polymicrobial bacteremia and sepsis. The perforation of the cecum allows the release of fecal material into the peritoneal cavity to generate an exacerbated immune response induced by polymicrobial infection. In this model, sepsis causes systemic activation of the inflammatory response, microvascular dysfunction, tissue hypoxia, multi-organ failure, and hemodynamic disorder that results in death as in clinical practice.

The animals are supported by subcutaneous fluid administration every 8 hours and administration of buprenorphine 0.1 mg/kg and paracetamol 300 mg/kg, as is the case with septic patients in the intensive care unit (ICU). All animals are closely monitored for their clinical status based on a modified score scale known as the Lipopolysaccharide (LPS) Score Sheet.

The animals divide into 2 groups: the first group receives placebo (placebo group) and the second group receives intraperitoneally a dose of 0.3 µg T3/g of body weight, immediately after surgery (group T3). Based on guidelines for converting doses from experimental animals to equivalent doses in humans (Nair, A B and Jacob S. A simple practice guide for dose conversion between animals and humans. I Basic C/in Pharma 2016, 7: 27-31), the dose of 0.3 µg T3/g of body weight, corresponds roughly to intravenous administration of 7 µg T3/Kg body weight, i.e., from 400 to 600 µg T3 for a patient weighing 60-80 Kg. This dose is very high and beyond any T3 treatment in hypothyroid patients. The study is performed in two separate experiments. In the first experimental protocol, the clinical condition of the animals and mortality after 72 hours is examined, while in the second experimental protocol, tissue hypoxia at the cellular level after euthanasia at 18 hours is studied.

Initially, lactate levels in blood samples are measured (using L-lactate assay kit from Sigma-Aldrich, MAK329) as a general indicator of hypoxia, which is also commonly used in clinical practice in patients with sepsis. Furthermore, creatinine levels in blood are measured as an indicator of renal function (using the Mouse Creatinine Kit Cat. 80350, Crystal Chem). Finally, an echocardiographic analysis is performed in order to evaluate the end-diastolic and end-systolic volume, the ejection fraction and the pulse volume according to the Simpson rule.

Echocardiographic analysis was performed after mild anesthesia with sevoflurane (0.8%) and placing the animal in a heated blanket. Echocardiographic images were then taken along the longitudinal and transverse sternal axis with the Vivid 7 version Pro ultrasound system (GE Healthcare, Wauwatosa, Wisconsin), equipped with a 14.0-MHz probe (i13L).

Tissue hypoxia at the cellular level is determined in frozen fixed tissues in 4% paraformaldehyde based on the standard method of pimonidazole administration using the Hypoxyprobe™ Plus kit. Pimonidazole is dissolved and administered intravenously in mice at a dose of 60 mg/kg, 2 hours before euthanasia. After intracardiac infusion with paraformaldehyde, the organs are fixed, removed and dehydrated for 5 days in 30% sucrose solution. Then, organs are immersed in OCT (Optimal cutting temperature compound) placed in a cryostat and cut into 20 µm-thick sections. Pimonidazole diffuses into cells and is reductively activated in hypoxic cells ($pO_2$<10 mm Hg) forming stable complexes with sulfhydryl groups of proteins, peptides and amino acids. These complexes are then detected by immunohistochemistry methods using specific antibodies and the dye DAB (3,3D-Diaminobenzidine) which provides a characteristic brown color. The images were taken under a microscope (Zeiss Axiovert) and automated image analysis was performed with ImageJ software to quantify the hypoxic area.

Figure 5A:
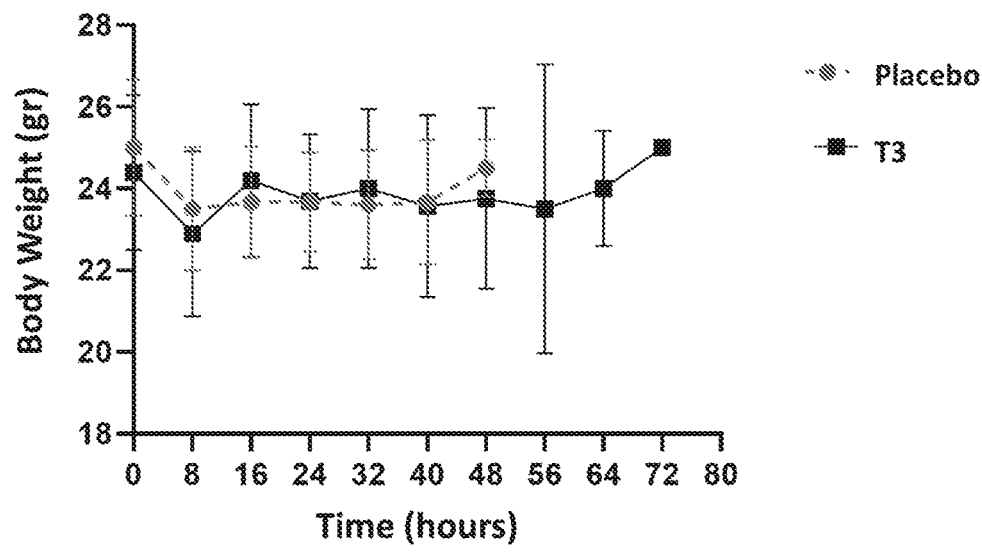
FIG. 5A shows body weight changes in placebo group and group T3.
Figure 5B:
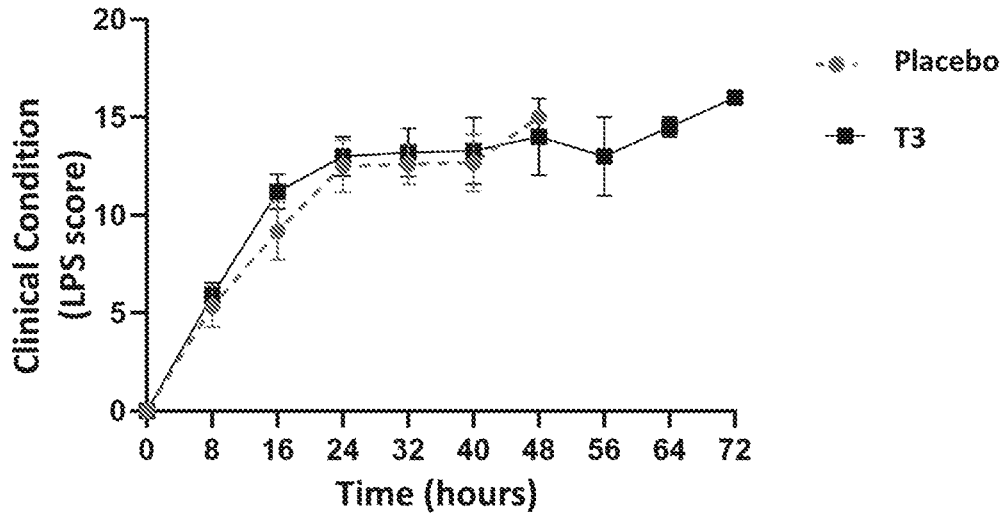
FIG. 5B shows changes in clinical condition (LPS scale) in placebo group and group T3.
Figure 5C:
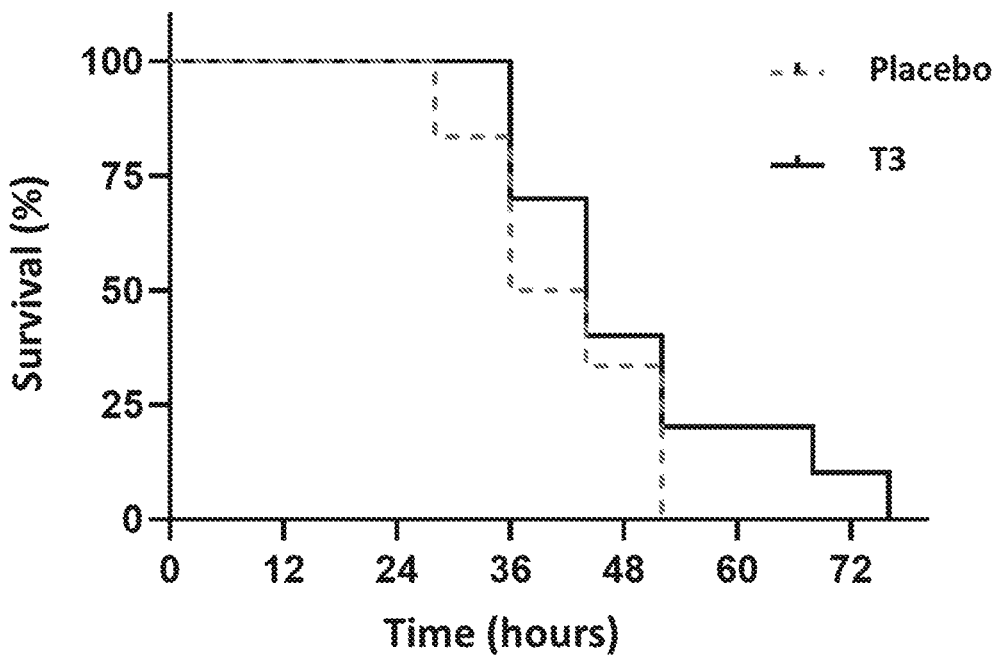
FIG. 5C shows animal survival after sepsis in placebo group and group T3.

Sepsis results in significant worsening in the clinical condition of the animals in the placebo group. Increased mortality is observed especially after the first 24 hours, while up to 72 hours all animals die. However, in the T3 group, there is a significant improvement in terms of mortality where up to 20% of animals survive at 72 hours (FIG. 5).

Figure 6A:
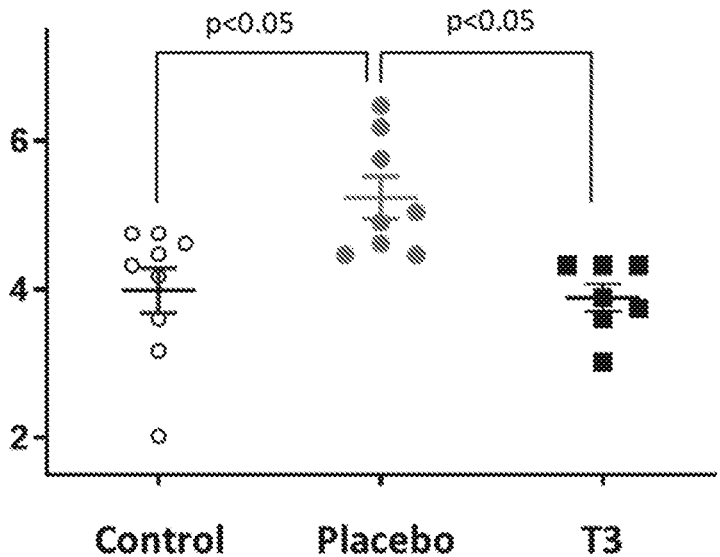
FIG. 6A shows lactic acid levels before surgery (Control) and after sepsis in the placebo group and the T3 group at 18 hours.
Figure 6B:
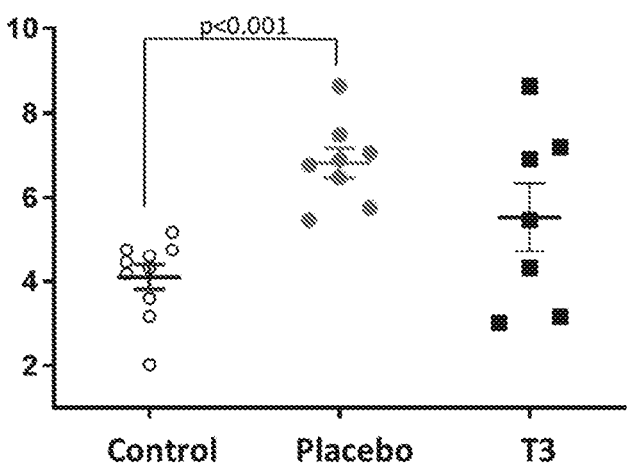
FIG. 6B shows lactic acid levels before surgery (Control) and after sepsis in the placebo group and the T3 group at 24 hours.

Sepsis further causes elevated lactate levels in blood in the placebo group at both 18 hours and 24 hours. Lactate is a known product of anaerobic metabolism, therefore, is considered an important general indicator of hypoxia. Unexpectedly, T3 administration led to a decrease in lactic acid levels at both 18 and 24 hours (FIG. 6).

Figure 7A:
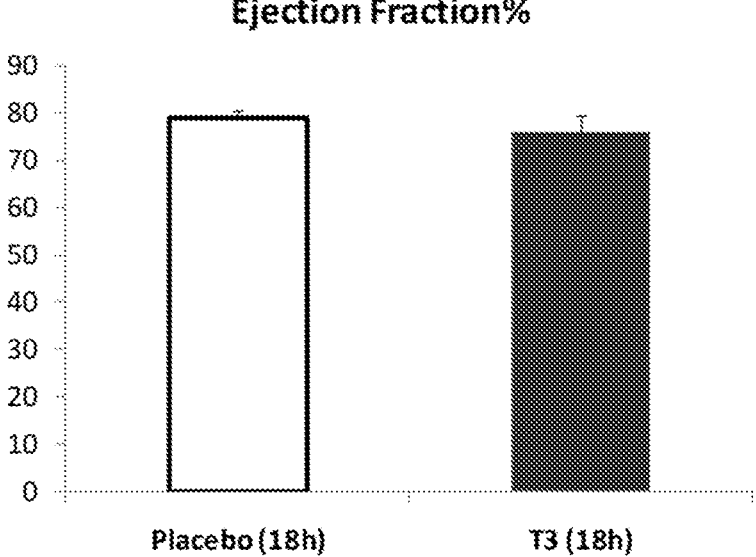
FIG. 7A illustrates the left ventricular ejection fraction at 18 hours after sepsis induction in the placebo group and in the 13 group as shown by echocardiogram analysis.
Figure 7B:
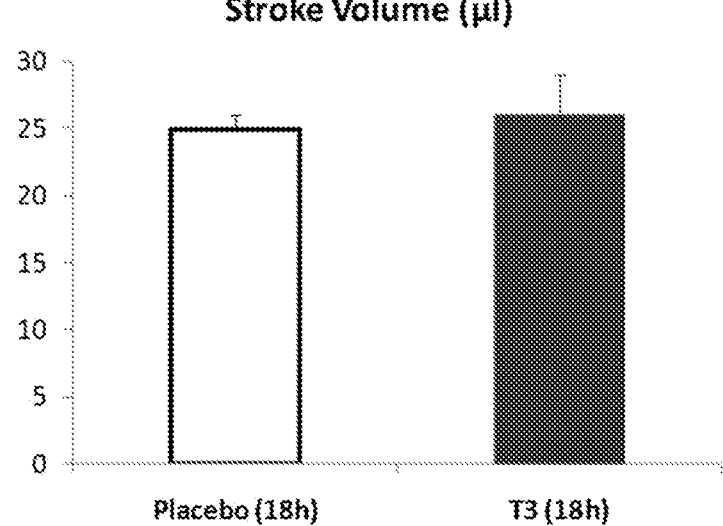
FIG. 7B illustrates the pulse volume at 18 hours after sepsis induction in the placebo group and in the T3 group as shown by echocardiogram analysis.

It is important to mention that the increase of lactate levels is observed despite the normal cardiac function as shown by echocardiography. Ejection fraction, pulse volume and heart rate are found to be within normal range, without any significant difference between the two groups studied, indicating that both cardiac output and perfusion at the macrocirculatory level are normal (FIG. 7).

Figure 8A:
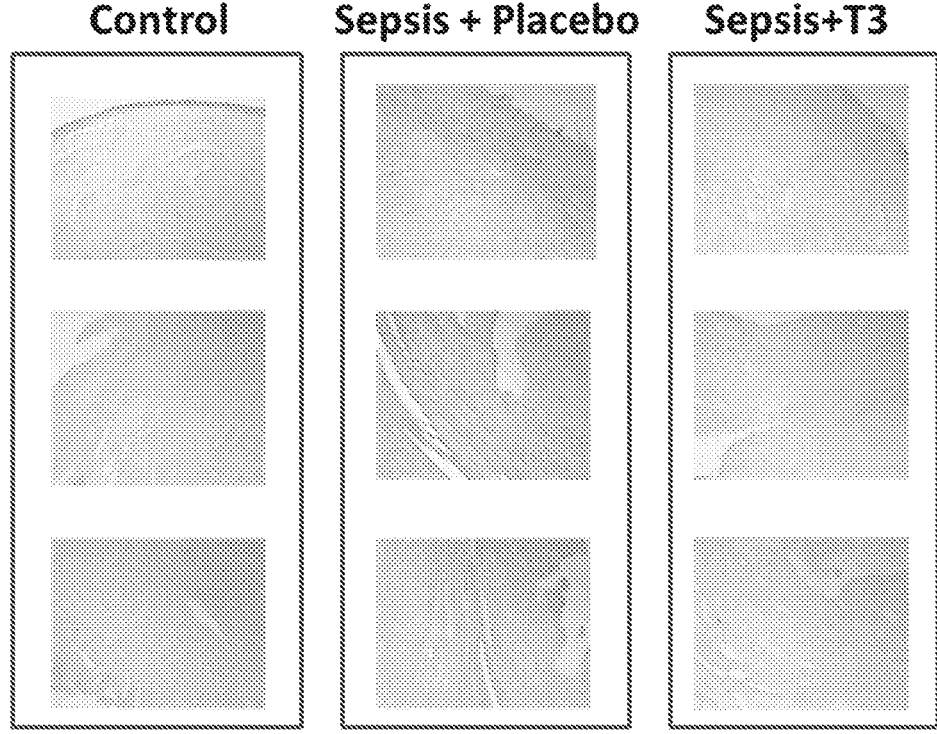
FIG. 8A shows representative microscope images showing myocardial tissue after tissue hypoxia labeled with pimonidazole (brown, intense imaging). It is presented: normal tissue (Control—left) as well as tissue from experimental animals that received placebo (center) and T3 (right).
Figure 8B:
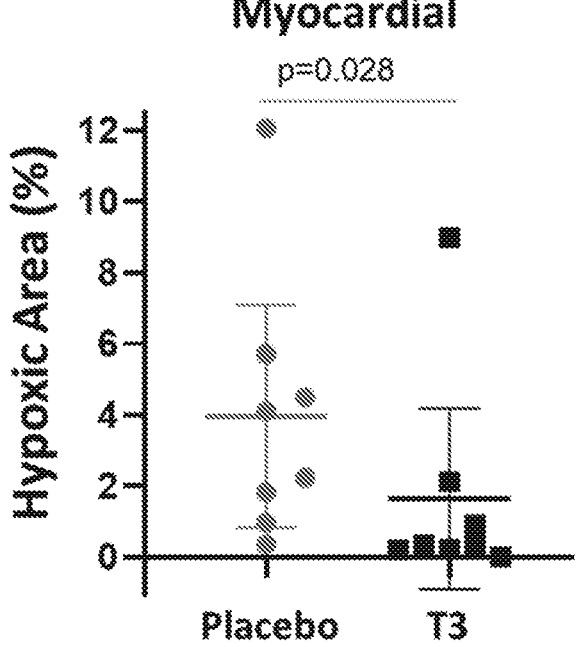
FIG. 8B shows the quantification of tissue hypoxia after image processing with special software.

The study of myocardial tissue hypoxia showed that in the placebo group of sepsis the tissue being positive reached an average of 4%±0.5 of the left ventricular total tissue, while T3 administration resulted in a statistically significant reduction in tissue hypoxia up to 1.5%±0.5, p=0.028 (FIG. 8).

Figure 9A:
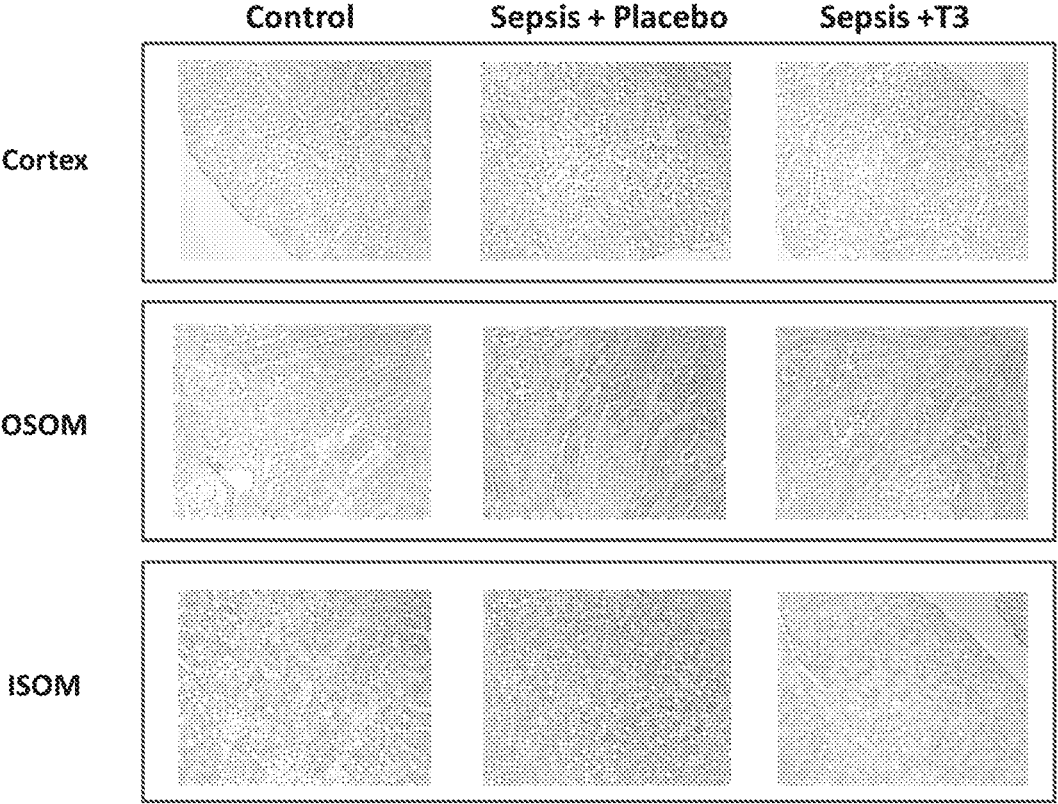
FIG. 9A shows representative microscope images showing renal tissue after labeling of tissue hypoxia with pimonidazole (brown, intense imaging) in different areas of the kidney (Cortex, OSOM, ISOM). It shows normal tissue (Control—left) as well as tissue from experimental animals that received placebo (center) and T3 (right).
Figure 9B:
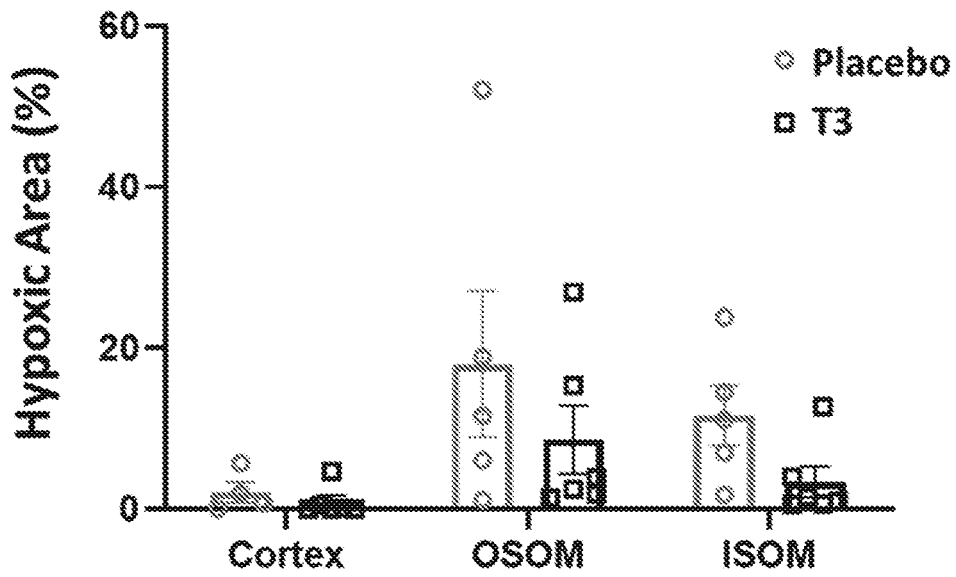
FIG. 9B shows a Diagram illustrating the quantification of tissue hypoxia after image processing with special software.

As regards the renal tissue hypoxia, it is observed that just 18 hours after sepsis, there is a significant increase in tissue hypoxia in the placebo group, especially in the areas of the renal tubules (outer stripe of the outer medulla—OSOM, and inner stripe of the outer medulla—ISOM) and less in cortex, while T3 administration manages to significantly reduce tissue hypoxia in these areas (OSOM and ISOM) (FIG. 9).

Figure 10:
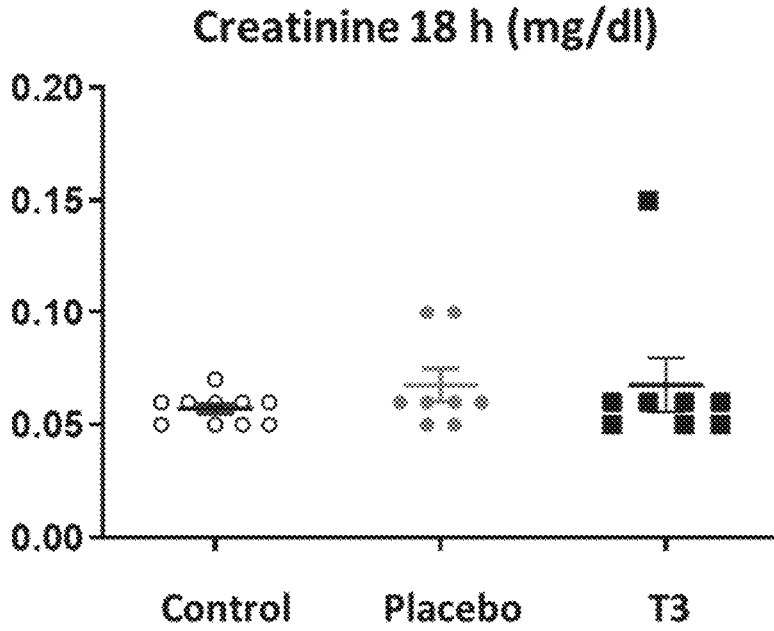
FIG. 10 shows serum creatinine levels before surgery (Normal) as well as 18 hours and 24 hours after sepsis in the placebo group and the T3 group.

In addition, creatinine levels did not increase in any of the groups at 18 hours, as damage of more than 50% of renal mass needs to occur to observe an increase in serum creatinine (FIG. 10).

Figure 11A:
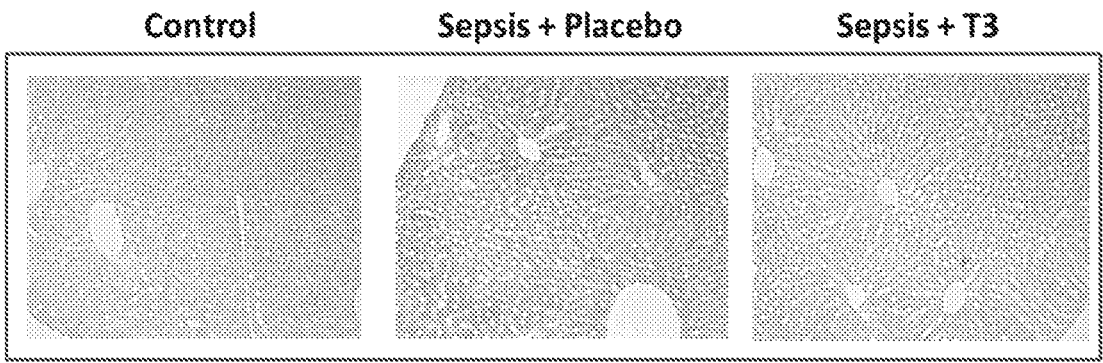
FIG. 11A shows representative microscope images showing liver tissue after labeling of tissue hypoxia with pimonidazole (brown, bright image). Normal tissue: Control—left; tissue from experimental animals that received placebo (center) and T3 (right).
Figure 11B:
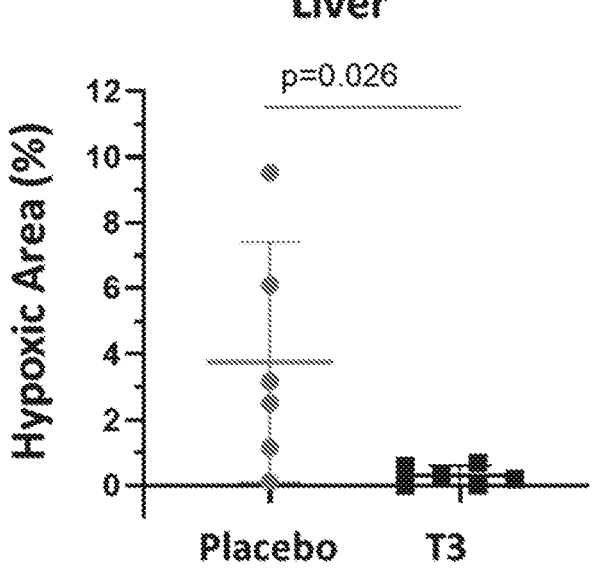
FIG. 11B shows the quantification of tissue hypoxia after image processing with special software.

Unexpected results are observed regarding the study of liver tissue hypoxia. Specifically, at 18 hours after sepsis, there is a significant increase in tissue hypoxia in the placebo group that is selectively located mainly around the hepatic venous regions, while 13 administration according to the current invention led to a statistically significant reduction in hepatic hypoxia (FIG. 11).

The above results indicate that high dose 13 treatment can prevent tissue hypoxia in cardiac, liver and kidney samples which occurs early in experimental sepsis (within 18 h) before cardiac output is impaired. Pimonidazole staining was used to detect tissue $pO_2$<10 mmHg. Oxygen below this level results in activation of Hypoxia inducible factor (HIF1α) dependent regulatory mechanisms which promote pathologic angiogenesis, changes in immune response and determine sepsis-induced injury progression. Thus, T3 treatment could regulate HIF1α dependent pathways via restoration of normal oxygen levels in tissue. T3 treatment was also shown to significantly lower circulating lactate levels probably due to the prevention of tissue hypoxia and microvascular dysfunction. However, favorable actions of T3 on cellular metabolism may also account for this effect. T3 can improve coupling of glycolysis to glucose oxidation and decrease $H^+$ production via its action on pyruvate dehydrogenase activity (PDH). PDH is found to be suppressed during sepsis (Nuzzo E, et al. Pyruvate dehydrogenase levels are low in sepsis. *Crit Care* 2015, 19:P33.)

The above-indicated results are better understood with reference to FIGS. 5 to 11.

FIG. 5 shows (a) body weight changes; (b) changes in clinical condition (LPS scale) and (c) animal survival after sepsis, in placebo group and group T3.

FIG. 6 shows lactic acid levels before surgery (Control) and after sepsis in the placebo group and the T3 group at (a) 18 hours and (b) 24 hours.

FIG. 7 illustrates (a) the left ventricular ejection fraction and (b) the pulse volume, at 18 hours after sepsis induction in the placebo group and in the T3 group as shown by echocardiogram analysis.

FIG. 8 shows: (a) representative microscope images showing myocardial tissue after tissue hypoxia labeled with pimonidazole (brown, intense imaging). It is presented: normal tissue (Control—left) as well as tissue from experimental animals that received placebo (center) and T3 (right); (b) the quantification of tissue hypoxia after image processing with special software.

FIG. 9 shows (a) representative microscope images showing renal tissue after labeling of tissue hypoxia with pimonidazole (brown, intense imaging) in different areas of the kidney (Cortex, OSOM, ISOM). It shows normal tissue (Control—left) as well as tissue from experimental animals that received placebo (center) and T3 (right). (b) Diagram illustrating the quantification of tissue hypoxia after image processing with special software.

FIG. 10 shows serum creatinine levels before surgery (Normal) as well as 18 hours and 24 hours after sepsis in the placebo group and the T3 group.

FIG. 11 shows (a) representative microscope images showing liver tissue after labeling of tissue hypoxia with pimonidazole (brown, bright image). Normal tissue: Control—left; tissue from experimental animals that received placebo (center) and T3 (right). (b) the quantification of tissue hypoxia after image processing with special software.

Example 3: Effect of High-Dose L-Triiodothyronine Administration in Critically Ill Patients with COVID-19 Infection This study (ThySupport, EudraCT: 2020-001623-13) is a phase II, parallel group, prospective, randomized, double-blind placebo-controlled study aiming to investigate the effect of intravenous T3 for the treatment of critically ill patients admitted to the intensive care unit (ICU) due to COVID-19 infection.

In particular, it refers to ICU patients diagnosed with pulmonary infection due to COVID-19 and require mechanical respiratory support or ECMO. Example 3 concerns the first results of this study.

The treatment begins with a relatively high dose immediately after the patient is intubated. This single dose (Bolus) may range from 0.6 µg/kg to 1.0 µg/kg body weight and most preferably is 0.8 µg/kg body weight. Thus, patients can receive a dose over a period of 2-3 minutes between 4.0 and 8.0 mL of a T3 solution containing 10 µg of L-triiodothyronine per 1 mL. This dose (bolus) can be given intravenously.

Subsequently, patients receive a continuous infusion for 24-72 hours, preferably for 48 hours after the bolus administration. Typically, patients receive T3 under continuous infusion at a rate from 0.1 to 0.2 µg/kg/h, preferably from 0.10 to 0.12 µg/Kg/h and most preferably receive 0.112 µg/kg/h for 48 hours.

After the first continuous infusion, in case is needed, patients may receive a second continuous infusion of T3 in the range from 0.025 to 0.08 µg/kg/h, preferably 0.056 µg/kg/h, until successful disconnection from the mechanical support or the end monitoring and for a maximum period of 30 days.

Figure 12:
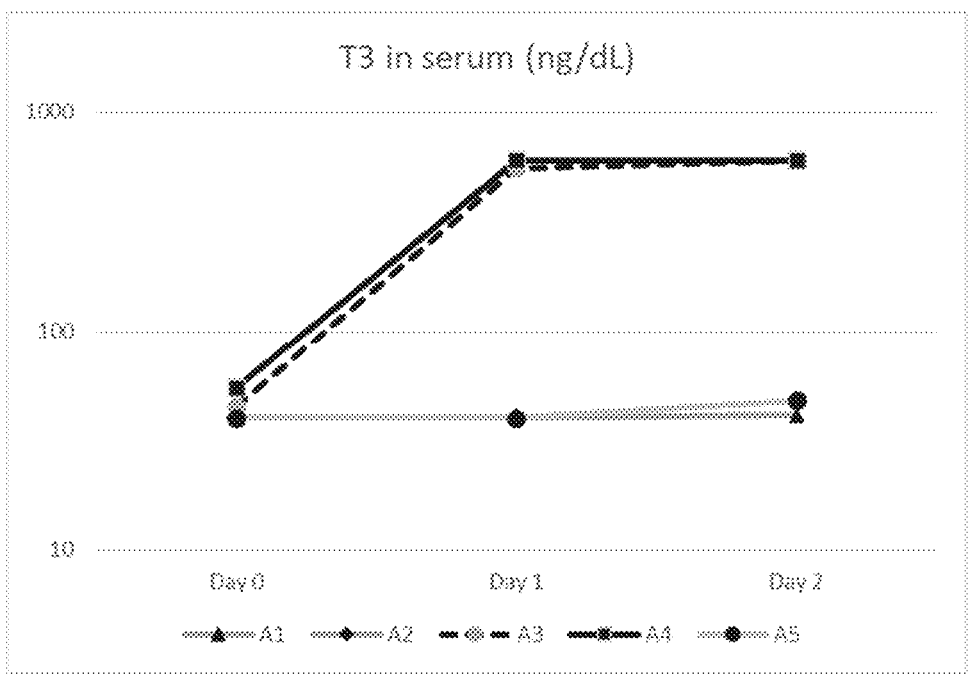
FIG. 12 shows T3 levels in blood for each patient in the first 48 hours after high dose T3 administration. (Patients A3 and A4 received T3, while A1, A2 and A5 received placebo).

T3 levels in blood increased as expected based on the dosage regimen and pharmacokinetic data as shown in FIG. 12.

Figure 13:
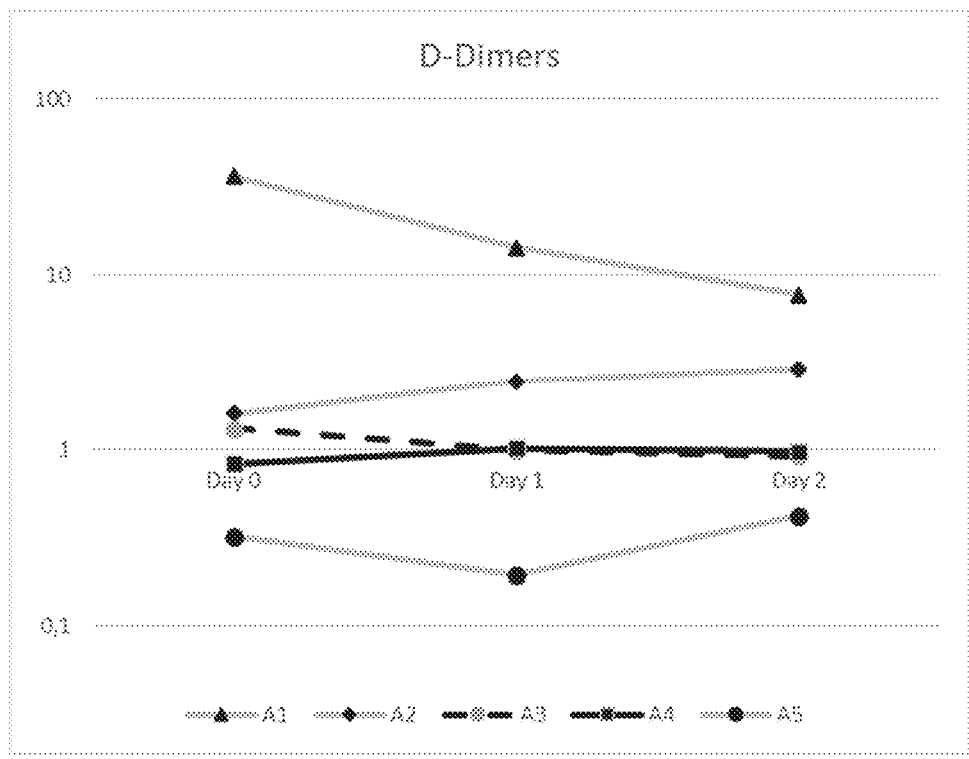
FIG. 13 shows d-dimers levels for each patient during the first 48 hours after high dose T3 administration. (Patients A3 and A4 received T3, while A1, A2 and A5 received placebo).

However, high dosages of T3 levels administered in accordance with the present invention do not cause adverse effects in patients as shown for example by levels of d-dimers, which remain unchanged for the first 48 hours after high-dose T3 administration (FIG. 13). D-dimers represent an indicator of coagulatory system activation and are associated with inflammatory response in patients with sepsis.

Effect of High Dose T3 Administration on the Heart

Figure 14:
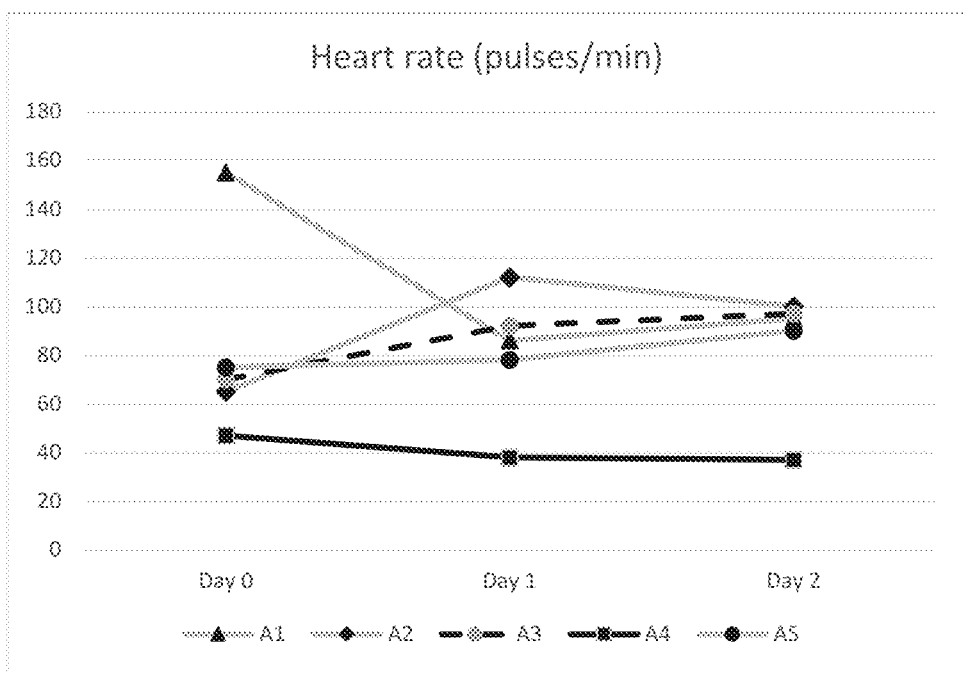
FIG. 14 shows the heart rate (pulses per minute) for each patient during the first 48 hours after high dose T3 administration. (Patients A3 and A4 received T3, while A1, A2 and A5 received placebo).

High-dose T3 administration did not induce significant tachycardia, atrial fibrillation, or ventricular arrhythmias (FIG. 14). High levels of thyroid hormones are linked to increased heart rate as well as causing certain arrhythmias such as atrial fibrillation. However, the preliminary results of the ThySupport study do not support such an effect in patients with severe COVID-19.

Figure 15:
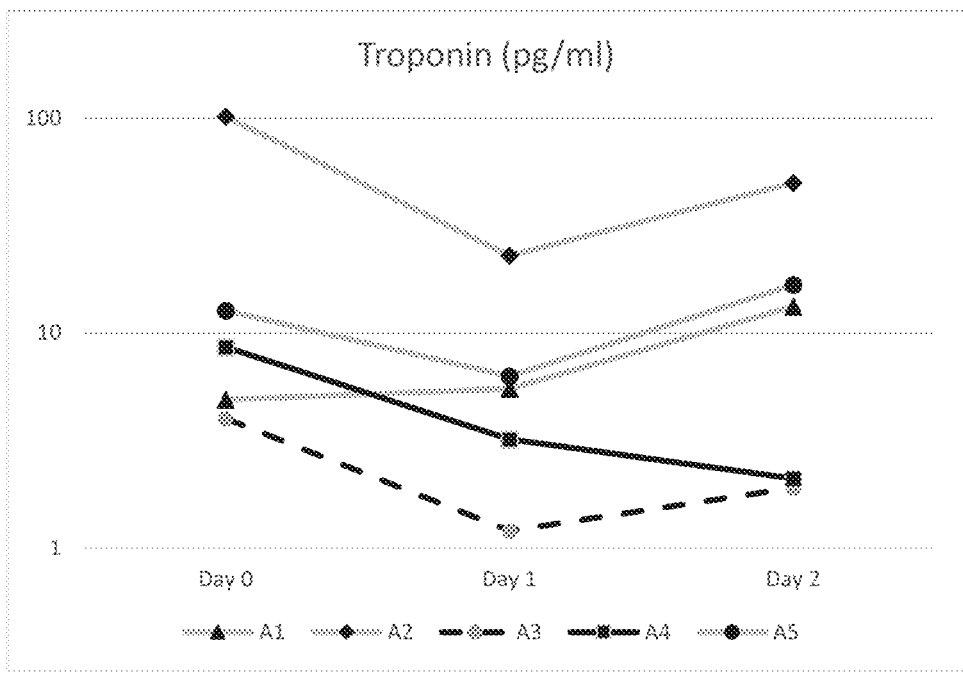
FIG. 15 shows the troponin I levels for each patient in the first 48 hours after high dose T3 administration. (Patients A3 and A4 received T3, while A1, A2 and A5 received placebo).

High-dose T3 administration was not accompanied by an increase in myocardial damage as assessed by troponin levels. Administration of high-dose T3 to patients with COVID-19 tends to decrease troponin compared to patients receiving placebo (FIG. 15). The cardioprotective effect of T3 on sepsis appears to be an important finding with significant therapeutic value concerning the outcome of these patients as myocardial damage increases mortality in COVID-19 patients based on recent studies.

Figure 16:
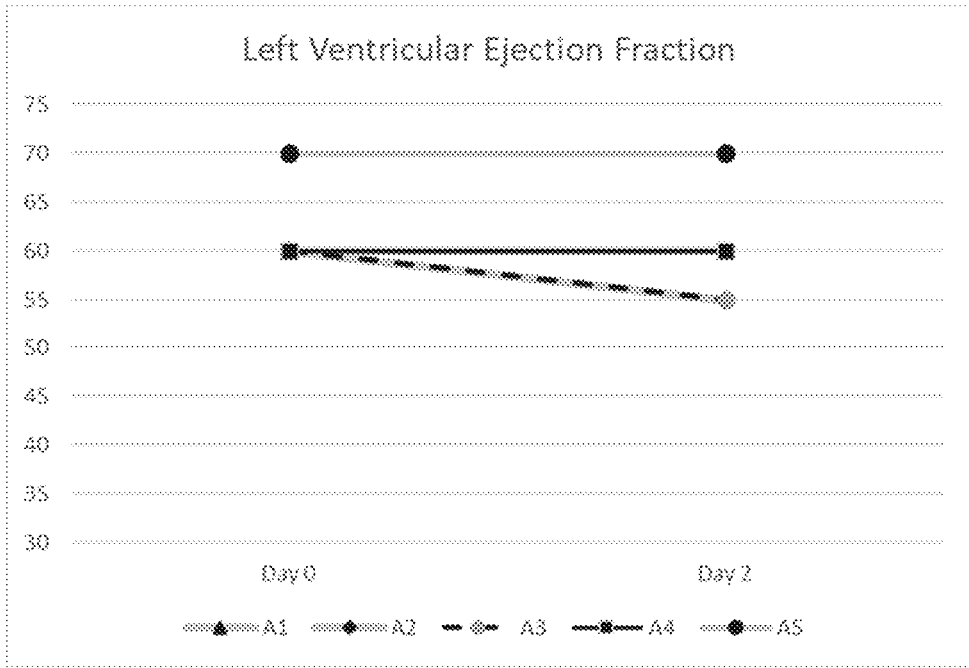
FIG. 16 shows the left ventricular ejection fraction for each patient in the first 48 hours after high dose T3 administration. (Patients A3 and A4 received T3, while A1, A2 and A5 received placebo).

High-dose T3 administration is related with an improvement in troponin levels, as well as maintenance of the function of left ventricle as assessed by the left ventricular ejection fraction (FIG. 16). Left ventricular function in these patients is crucial for maintaining a stable hemodynamic status.

Figure 17:
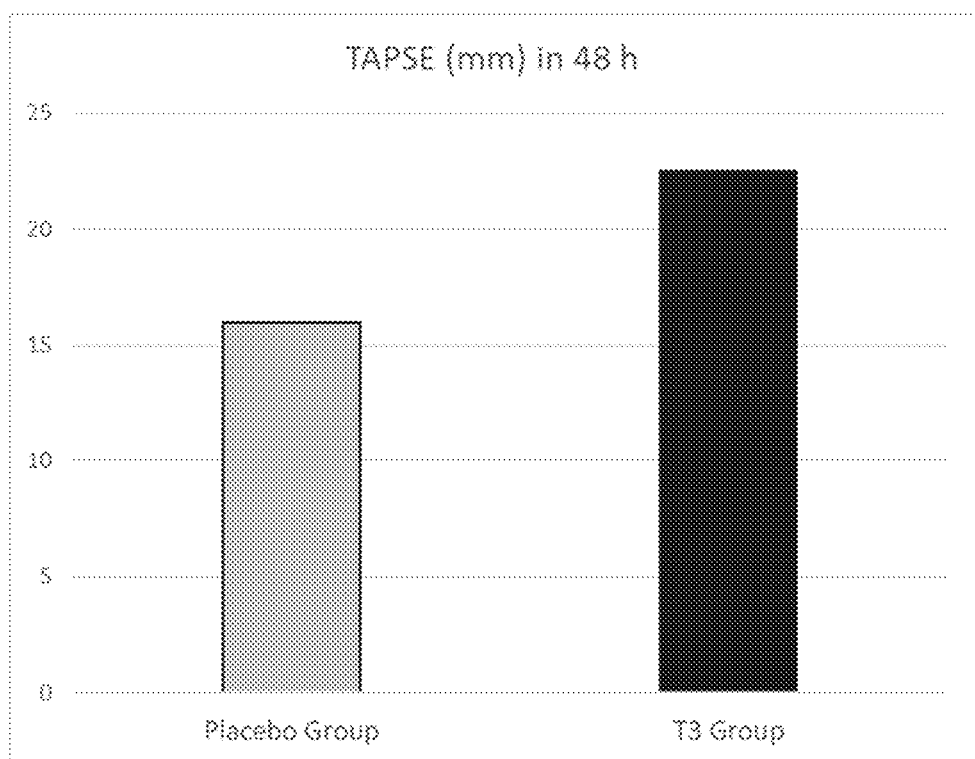
FIG. 17 shows the right ventricular systolic function at 48 hours after high-dose T3 administration.

High-dose T3 administration did not induce deterioration of right ventricular (RV) function but unexpectedly improved RV function (FIG. 17). The RV, which maintains blood flow to the lungs, is affected by sepsis and COVID-19 infection due to tissue changes that occur in the pulmonary parenchyma and result in increased resistance encountered by the RV. Furthermore, mechanical ventilation during intubation can further increase the resistance of the pulmonary vessels and impair the function of the right ventricle. These conditions created in sepsis can lead to right ventricular dysfunction associated with the inability of RV to respond to increased workload due to hypoxia (Right ventricular-arterial uncoupling).

According to these data, systolic pulmonary pressure (PASP), which is an indicator of right ventricular loading, was found to be similar between the two groups, while the inotropic condition of the right ventricle, as assessed by measuring displacement of the Tricuspid Annular Plane Systolic Excursion (TAPSE), shows an upward trend in patients after T3 administration. In addition, these patients exhibit low central venous pressure. The effect of T3 on right ventricular function in sepsis is an important finding as right heart failure is associated with high mortality in the first 28 days.

Figure 18:
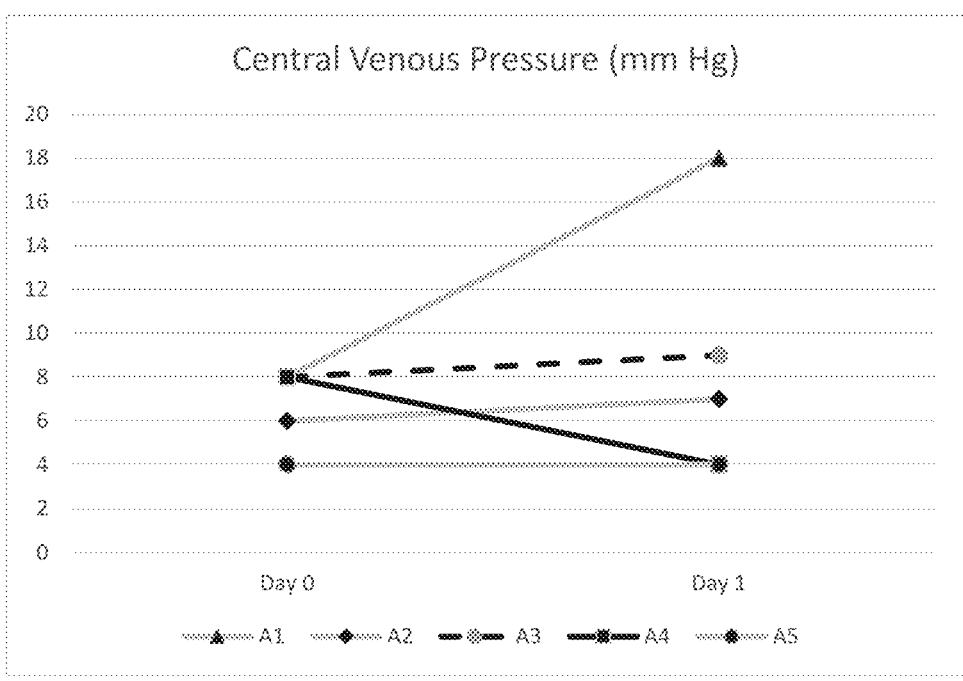
FIG. 18 shows the central venous pressure for each patient in the first 24 hours after high dose T3 administration. (Patients A3 and A4 received T3, while A1, A2 and A5 received placebo).

High dose T3 administration was not accompanied by an increase in central venous pressure during the first 24 hours, while it also showed a tendency to decrease. (FIG. 18). This finding is directly related to normal right ventricular function in patients in T3 group.

Effect of High Dose T3 Administration on Renal Function

Figure 19:
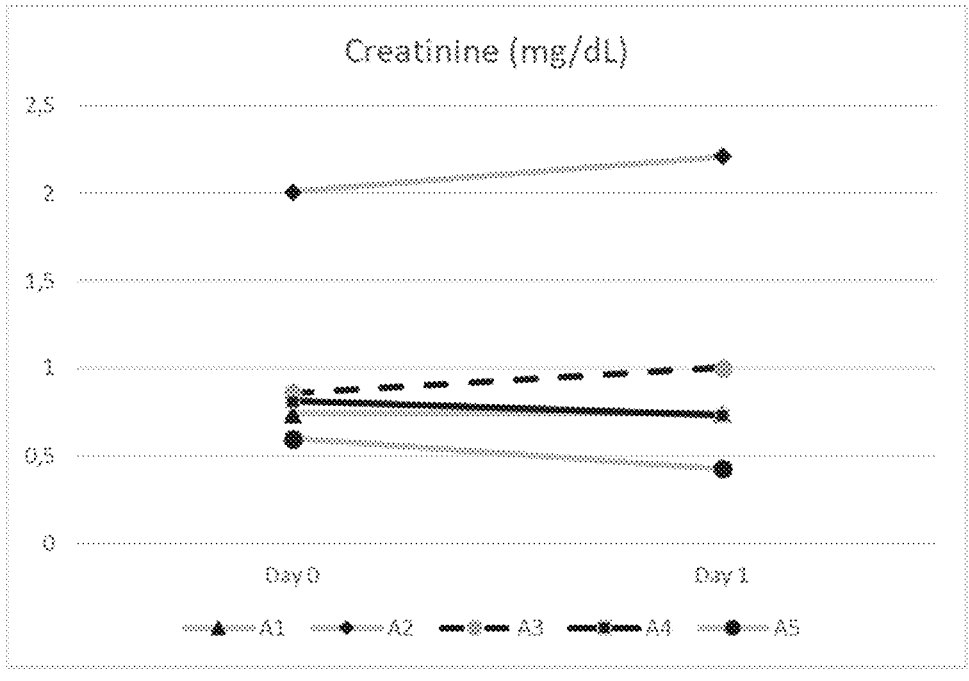
FIG. 19 shows creatinine levels for each patient in the first 24 hours after high dose T3 administration. (Patients A3 and A4 received T3, while A1, A2 and A5 received placebo).

Creatinine is an important indicator of kidney function. An increase in creatinine in critically ill patients with COVID-19 indicates possible hypoxic kidney damage due to sepsis and is a poor prognostic indicator. Laboratory tests have shown that high-dose T3 administration maintains normal renal function during the first 24 hours as shown by creatinine levels (FIG. 19).

Effect of High Dose T3 Administration on Liver Function

Figure 20:
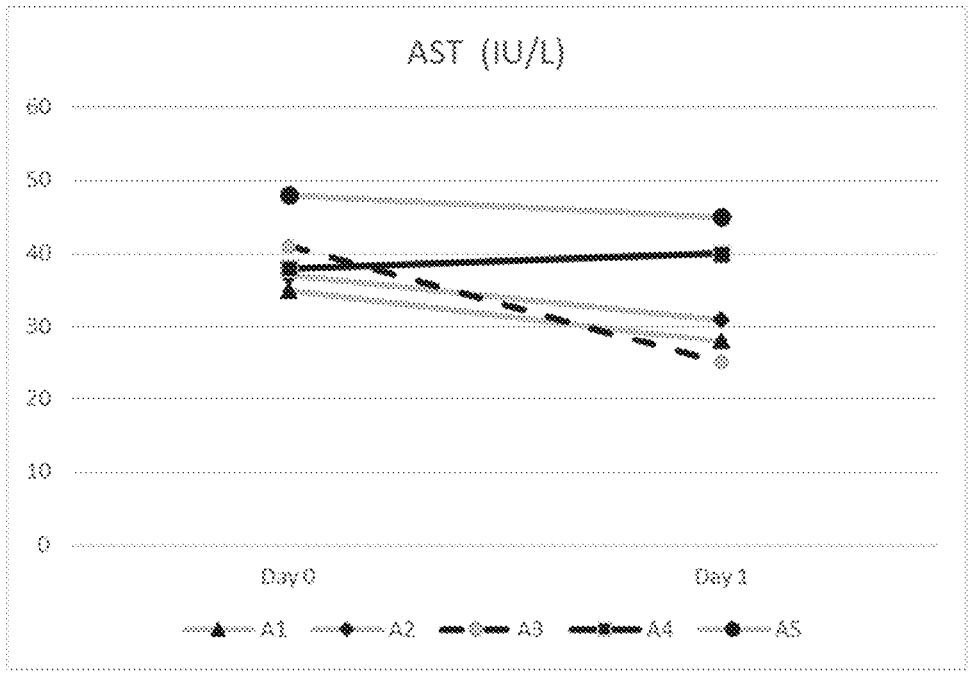
FIG. 20 shows the levels of liver enzymes for each patient in the first 24 hours after high dose T3 administration. (Patients A3 and A4 received T3, while A1, A2 and A5 received placebo).

Aspartate aminotransaminase (AST) is an important indicator of liver function. An increase in AST in critically ill patients with Covid-19 indicates possible hypoxic liver damage due to sepsis and is a poor prognostic indicator. Laboratory tests show that high-dose T3 maintains good patient liver function as shown by AST measurements during the first 24 hours (FIG. 20).

Effect of High Dose T3 Administration on Inflammatory Response

Figure 21:
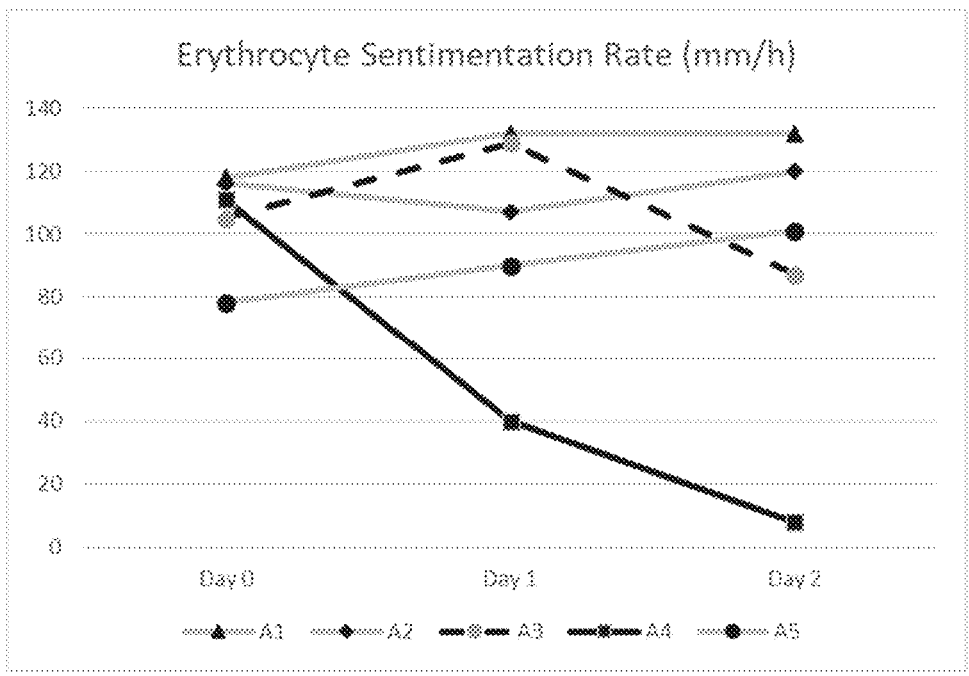
FIG. 21 shows the erythrocyte sedimentation rate levels for each patient in the first 48 hours after high dose T3 administration. (Patients A3 and A4 received T3, while A1, A2 and A5 received placebo).

Administration of a high dose of T3 according to the present invention did not worsen, but unexpectedly improved the inflammatory response as shown by erythrocyte sedimentation rate in the first 48 hours (FIG. 21).

Figure 22:
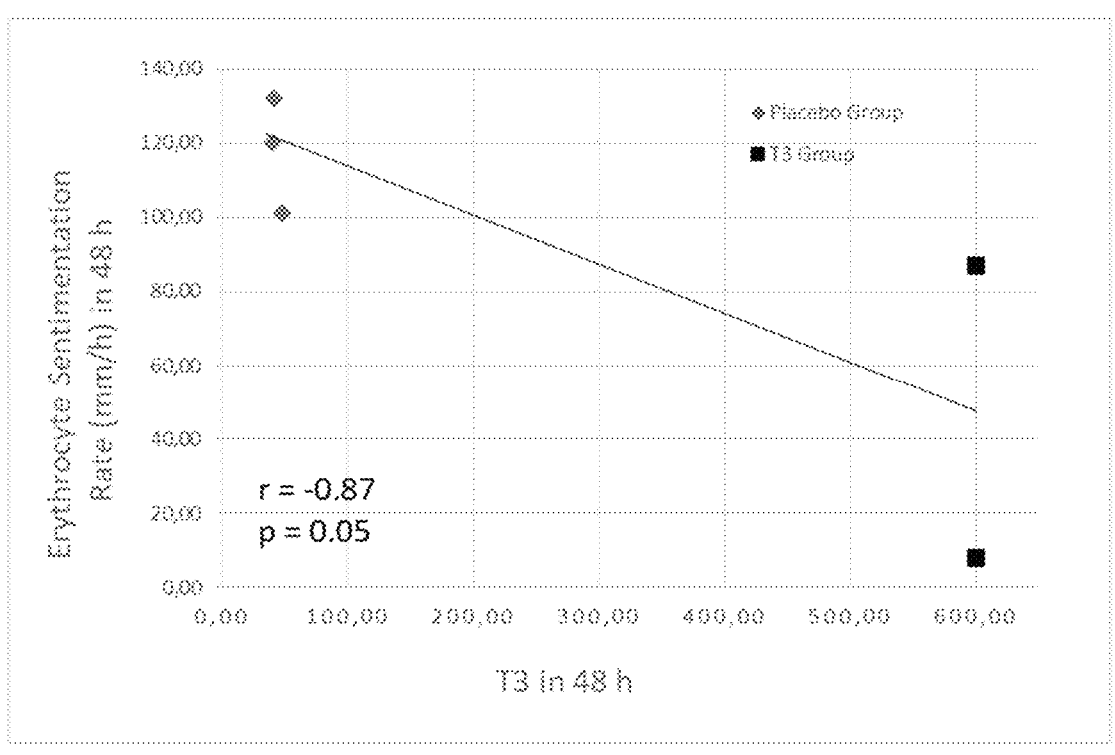
FIG. 22 shows erythrocyte sedimentation rate between patients receiving a high dose of T3 and patients receiving placebo.

Erythrocyte sedimentation rate remains an informative parameter of inflammation and haemorheologic abnormalities. Erythrocyte sedimentation rate reflects immune activation, altered plasma viscosity, enhanced red cell aggregation and impaired microvascular blood flow. Interestingly, erythrocyte sedimentation rate is shown to be associated with the severity of COVID-19 in which vasculitis is one of the main pathophysiological underlying mechanisms (Lapić I, et al. Erythrocyte sedimentation rate is associated with severe coronavirus disease 2019 (COVID-19): a pooled analysis. *Clin Chem Lab Med.* 2020, 58(7):1146-1148). Erythrocyte sedimentation rate has been a useful parameter in clinical practice to monitor drug therapies in various diseases. Here, we provide data showing that administration of T3 in ventilated COVID-19 patients resulted in an acute drop of erythrocyte sedimentation rate. Furthermore, the magnitude of erythrocyte sedimentation rate was strongly correlated to circulating T3 levels (FIG. 22). The potential of T3 administration to acutely reduce the erythrocyte sedimentation rate has not previously been described. This may reflect novel actions of T3 on inflammation and haemorheologic abnormalities. The latter may be of physiological relevance regarding tissue hypoxia.

The above-indicated results are better understood with reference to FIGS. 12 to 22 where:

FIG. 12 shows T3 levels in blood for each patient in the first 48 hours after high dose T3 administration. (Patients A3 and A4 received T3, while A1, A2 and A5 received placebo).

FIG. 13 shows d-dimers levels for each patient during the first 48 hours after high dose T3 administration. (Patients A3 and A4 received T3, while A1, A2 and A5 received placebo).

FIG. 14 shows the heart rate (pulses per minute) for each patient during the first 48 hours after high dose T3 administration. (Patients A3 and A4 received T3, while A1, A2 and A5 received placebo)

FIG. 15 shows the troponin I levels for each patient in the first 48 hours after high dose T3 administration. (Patients A3 and A4 received 13, while A1, A2 and A5 received placebo).

FIG. 16 shows the left ventricular ejection fraction for each patient in the first 48 hours after high dose T3 administration. (Patients A3 and A4 received 13, while A1, A2 and A5 received placebo).

FIG. 17 shows the right ventricular systolic function at 48 hours after high-dose T3 administration.

FIG. 18 shows the central venous pressure for each patient in the first 24 hours after high dose T3 administration. (Patients A3 and A4 received T3, while A1, A2 and A5 received placebo).

FIG. 19 shows creatinine levels for each patient in the first 24 hours after high dose T3 administration. (Patients A3 and A4 received T3, while A1, A2 and A5 received placebo).

FIG. 20 shows the levels of liver enzymes for each patient in the first 24 hours after high dose T3 administration. (Patients A3 and A4 received T3, while A1, A2 and A5 received placebo).

FIG. 21 shows the erythrocyte sedimentation rate levels for each patient in the first 48 hours after high dose T3 administration. (Patients A3 and A4 received T3, while A1, A2 and A5 received placebo).

FIG. 22 shows erythrocyte sedimentation rate between patients receiving a high dose of T3 and patients receiving placebo.

According to the present invention, administration of a high dose T3 to intubated COVID-19 patients is safe, without serious side effects, such as arrhythmias, pulmonary embolism, etc.

According to the present invention, administration of a high dose of T3 to patients with sepsis due to COVID-19 improves myocardial damage and right ventricular function while at the same time results in reduction of inflammatory response.

Example 4

A practitioner may consult the following explanation and tables, which show an example of dosage schedule of T3 administration according to a subject's weight.

TABLE 1

| Dosage schedules of T3 Solution for injection 10 µg/mL according to patient's weight | | | | |
|---|---|---|---|---|
| Patient weight | Bolus administration over 2-3 min | Continuous infusion | Pump rate (first 48 h) | Pump rate (from day 3 till end) |
| 66 Kg | 5.5 mL (55 µg) | 18 mL (180 µg) in 232 mL NaCl 0.9% | 10.4 mL/h | 5.2 mL/h |
| 70 Kg | 5.5 mL (55 µg) | 19 mL (190 µg) in 231 mL NaCl 0.9% | 10.4 mL/h | 5.2 mL/h |
| 74 Kg | 6 mL (60 µg) | 20 mL (200 µg) in 230 mL NaCl 0.9% | 10.4 mL/h | 5.2 mL/h |
| 77 Kg | 6 mL (60 µg) | 21 mL (210 µg) in 229 mL NaCl 0.9% | 10.4 mL/h | 5.2 mL/h |
| 81 Kg | 6.5 mL (65 µg) | 22 mL (220 µg) in 228 mL NaCl 0.9% | 10.4 mL/h | 5.2 mL/h |
| 85 Kg | 7.0 mL (70 µg) | 23 mL (230 µg) in 227 mL NaCl 0.9% | 10.4 mL/h | 5.2 mL/h |
| 89 Kg | 7.0 mL (70 µg) | 24 mL (240 µg) in 226 mL NaCl 0.9% | 10.4 mL/h | 5.2 mL/h |
| 92 Kg | 7.5 mL (75 µg) | 25 mL (250 µg) in 225 mL NaCl 0.9% | 10.4 mL/h | 5.2 mL/h |
| >95 Kg | 7.5 mL (75 µg) | 26 mL (260 µg) in 224 mL NaCl 0.9% | 10.4 mL/h | 5.2 mL/h |

As a more specific example, the practitioner may consider the following.

For a patient of 77 Kg of weight, a dose of 6 mL (60 µg) will be administered as a bolus intravenously over 2-3 min within 60 min of respiratory support initiation. Then, the patient for the next 24 hours will receive 21 mL of the product (total of 210 µg of T3) that will be diluted in NaCl 0.9% and administered with a pump at a steady flow rate of 10.4 mL/h for a total duration of 48 hours. From day 3 till successful weaning or end of follow-up, the patient will receive 50% of this dose, 10.5 mL of the product (total of 105 µg of T3) that will be diluted in NaCl 0.9% and administered with a pump at a steady flow rate of 5.2 mL/h.

Triiodothyronine in the study is used in the form of a T3 Solution for injection 10 µg/mL that contains 150 µg of L-triiodothyronine in a total volume of 15 mL per vial. The medicament is a solution containing the active substance Liothyronine sodium and other ingredients including dextran 70, NaOH 1 N and water for injection. Liothyronine sodium is synthesized in vitro. The medicament could also be supplied in the lyophilized form and reconstituted with water for injection or saline immediately prior to use.

Example of T3 Solution for Injection

| No | Name of ingredient(s) | Quantity/1 mL |
|---|---|---|
| | Active ingredient: | |
| 1. | Liothyronine sodium | 10.0 μg |
| | Other ingredient (s): | |
| 1. | Dextran 70 | 60.0 mg |
| 2. | NaOH 1N | q.s. pH 10 |
| 3. | Water for Injections | qs 1.0 |

The dose administered is 0.8 μg/kg intravenously bolus starting immediately after respiratory support initiation and followed by an infusion of 0.112 μg/kg/h intravenously for 48 hours. From day 3 till successful weaning or end of follow-up, the patient may receive of 0.056 μg/kg/h intravenously, if needed.

The invention claimed is:

1. A method of treating an inflammatory response or one or multi-organ dysfunction in a patient with tissue hypoxia and microvascular dysfunction caused by sepsis, severe injury, and/or extracorporeal organ protection, the method comprising: treating the patient's kidneys, liver, brain, heart, gastrointestinal system, haemopoietic system or coagulatory system using a pharmaceutical composition L-triiodothyronine consisting of or a pharmaceutically acceptable salt thereof, and one or more pharmaceutically acceptable excipients, wherein said pharmaceutical composition is administered to the patient in a range of 5 to 9 μg L-triiodothyronine or the pharmaceutically acceptable salt thereof per kg of the patient's body weight over a period of 48 hours.

2. The method according to claim 1, comprising treating the patient for prolonged hypoxia due to sepsis of at least 30 minutes.

3. The method according to claim 1, comprising treating the patient for right ventricular systolic function, wherein a Tricuspid Annular Plane Systolic Excursion (TAPSE) is between 16 and 30 mm.

4. The method according to claim 1, comprising treating the patient for right ventricular systolic function, wherein a value of central venous pressure is measured between 1 and 10 mm Hg.

5. The method according to claim 1, comprising treating the patient for inflammatory response and coagulatory system dysfunction, wherein a erythrocyte sedimentation rate is reduced by 50% over a period of 48 hours.

6. The method according to claim 1, wherein the L-triiodothyronine or the pharmaceutically acceptable salt thereof is formulated either as an injectable solution or as a lyophilized powder for reconstitution.

7. The method according to claim 6, wherein the L-triiodothyronine or the pharmaceutically acceptable salt thereof is present in the injectable solution at a concentration from 2 to 20 μg/mL.

8. The method according to claim 7, comprising administering the L-triiodothyronine or the pharmaceutically acceptable salt thereof to the patient as a continuous injection at a rate from 0.08 to 0.20 μg/kg/h for 48 hours.

9. The method according to claim 7, comprising administering the L-triiodothyronine or the pharmaceutically acceptable salt thereof to the patient as an initial bolus from 0.6 to 1.0 μg L-triiodothyronine per kg of body weight followed by a continuous injection at a rate from 0.10 to 0.20 μg/kg/h for 48 hours.

10. The method according to claim 7, comprising administering the L-triiodothyronine or the pharmaceutically acceptable salt thereof to the patient intravenously in a total amount from 375 μg to 675 μg, based on a body weight of the patient of 75 kg.

11. The method according to claim 1 comprising administering the pharmaceutical composition to the patient in a range of 6 to 8 μg L triiodothyronine or the pharmaceutically acceptable salt thereof per kg of the patient's body weight.

12. The method according to claim 2 wherein the prolonged hypoxia due to sepsis is for at least 3 hours.

13. The method according to claim 3 wherein the TAPSE is between 20 and 25 mm.

14. The method according to claim 4 wherein the central venous pressure is measured between 3.7 and 7.4 mm Hg.

15. The method according to claim 5 wherein the erythrocyte sedimentation rate is measured below 30 mm within the first hour.

16. The method according to claim 7 wherein the concentration of the injectable solution is from 5 to 15 μg/mL.

17. The method according to claim 8 wherein the injection rate is from 0.12 to 0.16 μg/kg/h.

18. The method according to claim 9 wherein the continuous injection rate is 0.10 to 0.14 μg/kg/h.

19. The method according to claim 10 wherein the patient receives 450 to 600 μg L triiodothyronine or the pharmaceutically acceptable salt thereof in total.

* * * * *